United States Patent
Oplinger et al.

(10) Patent No.: US 11,418,897 B2
(45) Date of Patent: Aug. 16, 2022

(54) EAR CANAL MICROPHONE UTILIZING COMMUNICATIONS WITH HEARING IMPLANT

(71) Applicant: Cochlear Limited, Macquarie University (AU)

(72) Inventors: Kenneth Oplinger, Macquarie University (AU); Sören Nilsson, Mölnlycke (SE)

(73) Assignee: Cochlear Limited, Macquarie University (AU)

(*) Notice: Subject to any disclaimer, the term of this patent is extended or adjusted under 35 U.S.C. 154(b) by 121 days.

(21) Appl. No.: 16/960,518

(22) PCT Filed: Jan. 11, 2019

(86) PCT No.: PCT/IB2019/050204
§ 371 (c)(1),
(2) Date: Jul. 7, 2020

(87) PCT Pub. No.: WO2019/142079
PCT Pub. Date: Jul. 25, 2019

(65) Prior Publication Data
US 2020/0374638 A1      Nov. 26, 2020

Related U.S. Application Data

(60) Provisional application No. 62/617,853, filed on Jan. 16, 2018.

(51) Int. Cl.
*H04R 25/00*     (2006.01)

(52) U.S. Cl.
CPC .......... *H04R 25/554* (2013.01); *H04R 25/606* (2013.01)

(58) Field of Classification Search
CPC ............... H04R 25/554; H04R 25/606; H04R 2225/67; A61N 1/36038
See application file for complete search history.

(56) References Cited

U.S. PATENT DOCUMENTS 6,067,474 A       5/2000   Schulman et al.
6,157,727 A *    12/2000   Rueda .................... H04R 25/55
                                                             381/312

(Continued)

FOREIGN PATENT DOCUMENTS

| KR | 10-1648840 B1 | 8/2016 | |
| WO | WO-2009056167 A1 * | 5/2009 | ........... H04R 25/554 |
| WO | WO 2019/142079 A1 | 7/2019 | |

OTHER PUBLICATIONS

B.C. Towe, "Passive Backscatter Biotelemetry for Neural Interfacing," Proc. 3rd Int'l IEEE EMBS Conf. on Neural Engineering, Kohala Coast, Hawaii, USA, May 2-5, 2007, ThD1.20, pp. 144-147, (2007).

(Continued)

*Primary Examiner* — Phylesha Dabney
(74) *Attorney, Agent, or Firm* — Knobbe, Martens, Olson & Bear, LLP

(57) ABSTRACT

An apparatus includes a housing configured to be positioned within an ear canal of a recipient, at least one transducer, and at least one communication circuit. The at least one transducer is configured to respond to sound within the ear canal by generating output signals indicative of the sound. The at least one communication circuit has at least one resonance frequency and is configured to receive the output signals from the at least one transducer and to modulate the at least one resonance frequency in response to the output signals from the at least one transducer.

26 Claims, 19 Drawing Sheets

(56) References Cited

U.S. PATENT DOCUMENTS

| 9,392,381 B1* | 7/2016 | Park .................... H04R 25/556 |
| 2005/0111681 A1* | 5/2005 | Essabar .................. H04B 5/02 |
| | | 381/315 |
| 2015/0025613 A1 | 1/2015 | Nyberg, II et al. |
| 2016/0165364 A1* | 6/2016 | Flood ..................... H03H 7/38 |
| | | 381/315 |
| 2017/0180885 A1 | 6/2017 | Meskens et al. |

OTHER PUBLICATIONS

International Search Report and Written Opinion, Application No. PCT/IB2019/050204, dated May 13, 2019, in three (3) pages.

* cited by examiner

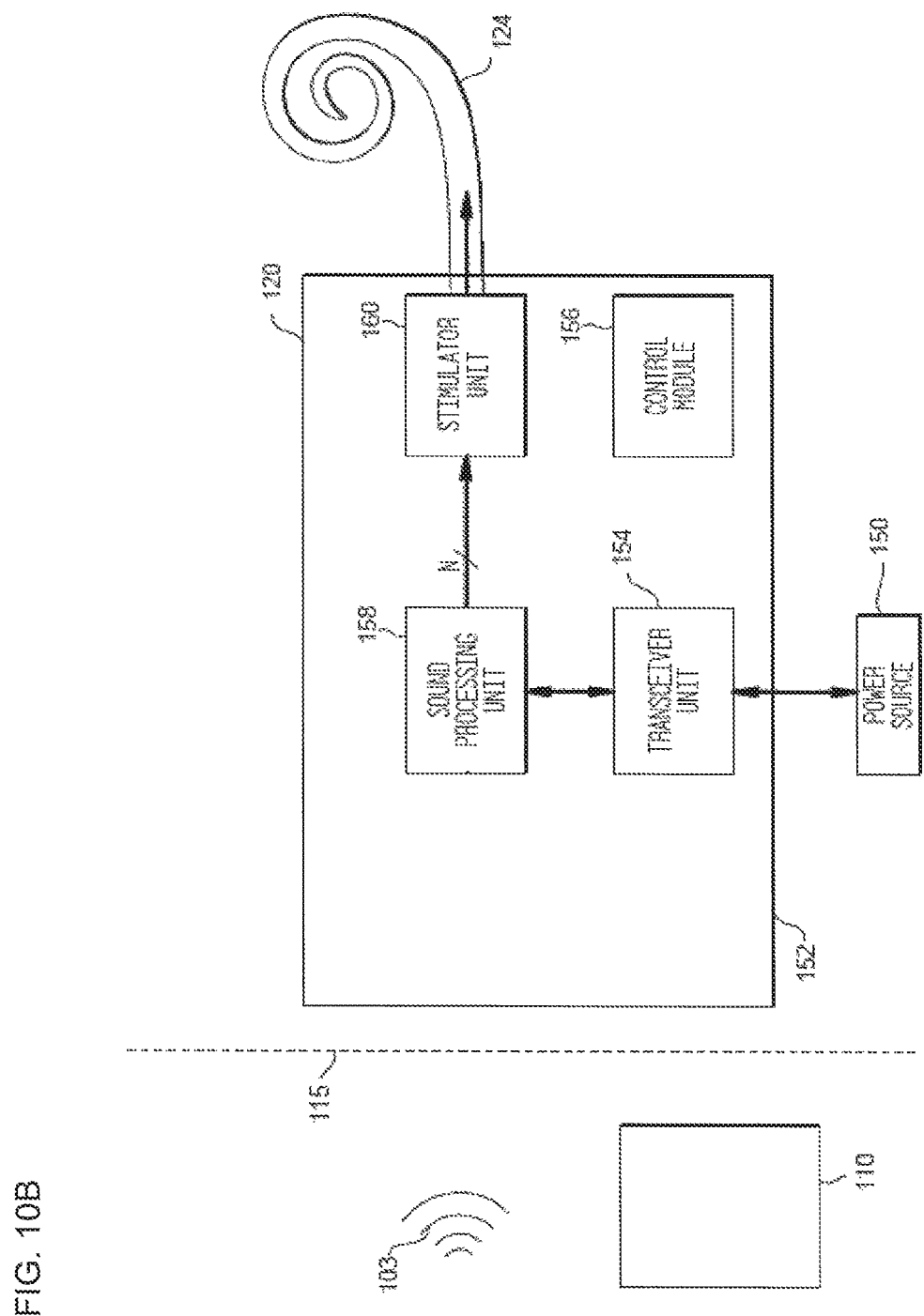

EAR CANAL MICROPHONE UTILIZING COMMUNICATIONS WITH HEARING IMPLANT

BACKGROUND

Field

The present application relates generally to auditory prostheses, and more particularly to implantable auditory prostheses.

Description of the Related Art

Various auditory prostheses utilize microphones that are positioned outside the ear canal (e.g., on the ear; off the ear; implanted under the skin behind the ear).

SUMMARY

In one aspect disclosed herein, an apparatus is provided which comprises a housing configured to be positioned within an ear canal of a recipient, at least one transducer, and at least one communication circuit. The at least one transducer is positioned on or within the housing, and is configured to respond to sound within the ear canal by generating output signals indicative of the sound. The at least one communication circuit has at least one resonance frequency and is positioned on or within the housing. The at least one communication circuit is configured to receive the output signals from the at least one transducer and to modulate the at least one resonance frequency in response to the output signals from the at least one transducer.

In another aspect disclosed herein, an apparatus is provided which comprises at least one transmission circuit, at least one detection circuit, and at least one excitation assembly. The at least one transmission circuit is configured to wirelessly transmit first electromagnetic signals to a transducer assembly positioned within an ear canal of a recipient. The at least one detection circuit is configured to detect second electromagnetic signals radiated from the transducer assembly, the second electromagnetic signals comprising a portion of the first electromagnetic signals reflected from the transducer assembly. The at least one excitation assembly is configured to generate excitation signals in response to the second electromagnetic signals.

In still another aspect disclosed herein, a method is provided which comprises receiving sound at an assembly within an ear canal of a recipient. The method further comprises wirelessly receiving first electromagnetic signals at the assembly within the ear canal. The method further comprises, in response to the received sound, applying modulations to at least a portion of second electromagnetic signals being radiated from the assembly.

In another aspect disclosed herein, an apparatus is provided which comprises at least one implantable communication circuit configured to wirelessly receive signals from a transducer assembly positioned within an ear canal of a recipient or externally to the recipient. The at least one communication circuit is further configured to generate at least one detection signal indicative of the wirelessly received signals from the transducer assembly. The apparatus further comprises at least one implantable control circuit configured to receive the at least one detection signal and, in response to the at least one detection signal, to perform one or more of the following: switch between a first state and a second state, wherein the at least one implantable control circuit in the first state is configured to control the apparatus to use a first level of power, the at least one implantable control circuit in the second state is configured to control the apparatus to use a second level of power less than the first level of power; transmit a corresponding alert to a destination external to the apparatus; and source one or more alternative transducer assemblies, wherein each of the one or more alternative transducer assemblies is separate from the transducer assembly positioned within the ear canal of the recipient or externally to the recipient.

BRIEF DESCRIPTION OF THE DRAWINGS

Embodiments are described herein in conjunction with the accompanying drawings, in which:

FIGS. 10A and 10B schematically illustrate an example MICI in accordance with certain embodiments described herein.

DETAILED DESCRIPTION

Figure 1:
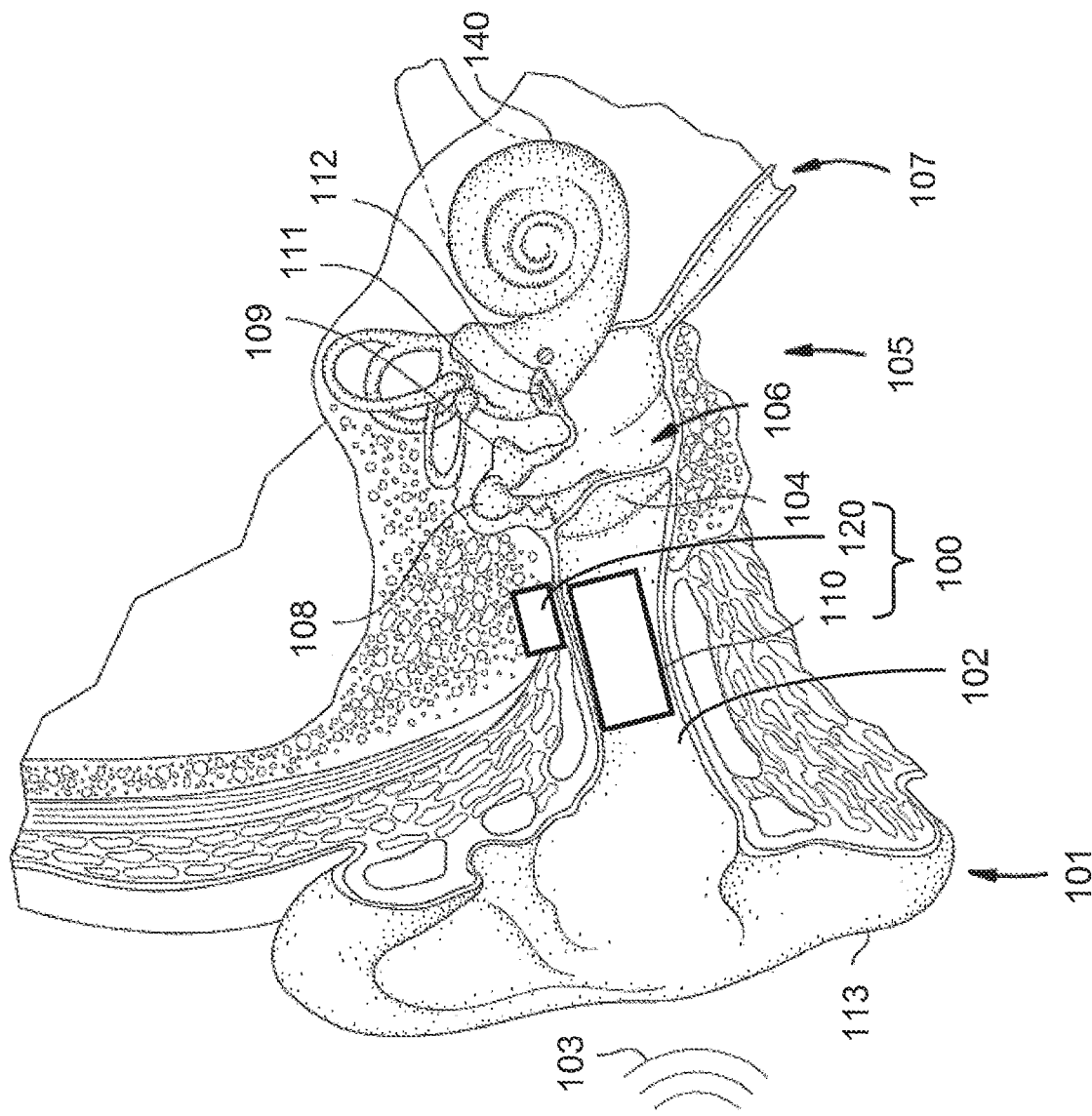
FIG. 1 schematically illustrates an example auditory prosthesis compatible with certain embodiments described herein.

FIG. 1 schematically illustrates an example auditory prosthesis 100 (e.g., a cochlear implant; a bone conduction auditory prosthesis; a middle ear auditory prosthesis; an auditory brainstem implant; a direct acoustic stimulator prosthesis; any combination thereof) compatible with certain embodiments described herein. The example auditory prosthesis 100 comprises an in-the-ear-canal ("ITEC") microphone 110 configured to be positioned within the ear canal 102 of the recipient and an implantable excitation device 120 that is configured to be capable of wireless communication with the ITEC microphone 110 and capable of operative communication with a portion of the recipient's auditory system. The ITEC microphone 110 is configured to generate information indicative of sound detected within the ear canal 102 (e.g., using a passive microphone such as a piezoelectric microphone) and to use backscatter communications for wirelessly transmitting the information to the implantable excitation device 120. The implantable excitation device 120 is configured to generate excitation signals in response to the information wirelessly received from the ITEC microphone 110 and to transmit the excitation signals to the recipient's auditory system (e.g., using one or more electrodes and/or actuators, not shown in FIG. 1).

The ITEC microphone 110 of certain embodiments described herein advantageously utilizes low or no power (e.g., not drawing power from a battery or other on-board power storage device), both in generating the information indicative of the detected sound (e.g., by virtue of using a piezoelectric microphone to detect the sound) and in transmitting the information to the implantable excitation device 120 (e.g., by virtue of using backscatter communications for wirelessly transmitting the information). The ITEC microphone 110 of certain embodiments advantageously does not use multiple microphones or power-hungry signal processing (e.g., which also utilizes memory and clock cycles), which are otherwise used with typical microphones that are positioned outside the ear canal 102 (e.g., on the ear; off the ear; implanted under the skin behind the ear), to replace the directionality naturally provided by the outer ear 101 and the ear canal 102. In contrast to implanted (e.g., subcutaneous) microphones, certain embodiments described herein advantageously do not exhibit performance degradation and/or challenges due to sound detected having to pass through skin tissue. In addition, the ITEC microphone 110 of certain embodiments is used without the surgical and implant component complexity of implanted microphones. Certain embodiments described herein provide continuous analog signal transfer between the ITEC microphone 110 and the implantable excitation device 120, bandwidths as high as 10 kHz, signal levels from microvolts to millivolts, high input impedances, little or no latency, and low cost.

As used herein, a recipient's auditory system includes all sensory system components used to perceive a sound signal, such as hearing sensation receptors, neural pathways, including the auditory nerve and spiral ganglion, and the regions of the brain used to sense sound. For example, as shown in FIG. 1, the recipient's auditory system can include, but is not limited to, an outer ear 101 (e.g., comprising an auricle 113), an ear canal 102, a tympanic membrane 104, a middle ear 105, three bones (e.g., the malleus 108, the incus 109, and the stapes 111, collectively referred to as the ossicles 106) of middle ear 105, an inner ear 107, an oval window or fenestra ovalis 112, and a cochlea 140. In a fully functioning auditory system, an acoustic pressure or sound wave 103 is collected by auricle 113 and channeled into and through ear canal 102. Disposed across the distal end of ear canal 102 is tympanic membrane 104 which vibrates in response to sound waves 103. This vibration is coupled to oval window 112 through the ossicles 106 which serve to filter and amplify sound waves 103, causing oval window 112 to articulate, or vibrate in response to vibration of tympanic membrane 104. This vibration sets up waves of fluid motion of the perilymph within cochlea 140. Such fluid motion, in turn, activates tiny hair cells (not shown) inside of cochlea 140. Activation of the hair cells causes appropriate nerve impulses to be generated and transferred through the spiral ganglion cells (not shown) and auditory nerve to the brain (not shown) where they are perceived as sound. An auditory prosthesis in accordance with certain embodiments described herein provides a functionality which replaces or supplements a missing or malfunctioning aspect of a recipient's non-fully functioning auditory system.

Figure 2:
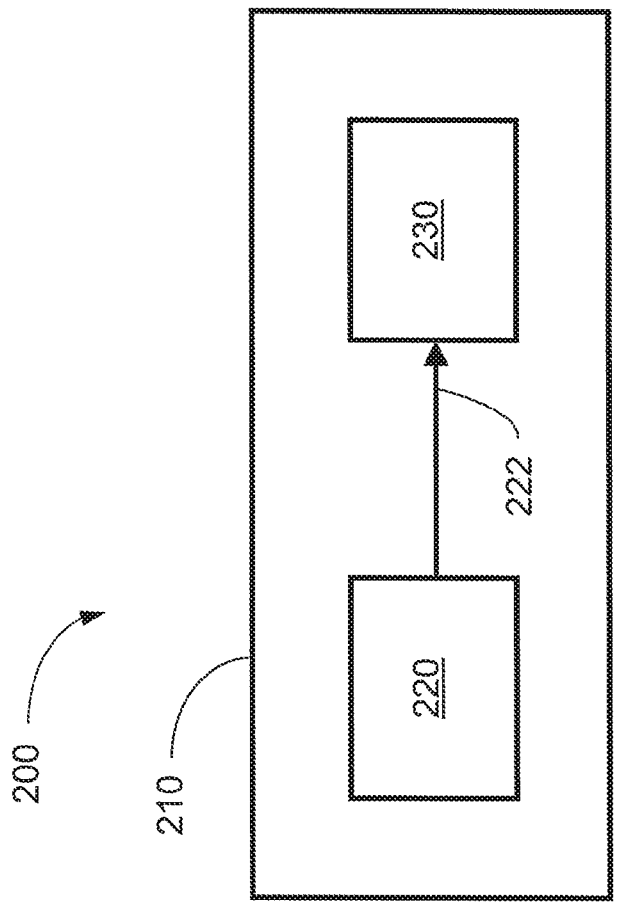
FIG. 2 schematically illustrates an example apparatus (e.g., an ITEC microphone) compatible with certain embodiments described herein.

FIG. 2 schematically illustrates an example apparatus 200 (e.g., an ITEC microphone 110) compatible with certain embodiments described herein. The apparatus 200 comprises a housing 210 configured to be positioned within an ear canal 102 of a recipient. The apparatus 200 further comprises at least one transducer 220 positioned on or within the housing 210. The at least one transducer 220 is configured to respond to sound within the ear canal 102 by generating output signals 222 indicative of the sound. The apparatus 200 further comprises at least one communication circuit 230 having at least one resonance frequency. The at least one communication circuit 230 is positioned on or within the housing 210. The at least one communication circuit 230 is configured to receive the output signals 222 from the at least one transducer 220 and to modulate the at least one resonance frequency in response to the output signals 222 from the at least one transducer 220.

In certain embodiments, the housing 210 is configured to be repeatedly inserted into and positioned within the ear canal 102 of the recipient (e.g., by the recipient or user; prior to operation of the apparatus 200) and repeatedly removed from the ear canal 102 (e.g., by the recipient or user; for cleaning or maintenance of the apparatus 200). The housing 210 can be configured to be comfortably worn within the ear canal 102 by the recipient for an extended period of time (e.g., hours; days; weeks; etc.) while remaining substantially stationary relative to the ear canal 102 (e.g., not appreciably moving within the ear canal 102 despite accelerations or other movements of the recipient's head). In certain embodiments, the housing 210 has a shape which conforms to the shape of the portion of the ear canal 102 in which the housing 210 is intended to reside during operation. For example, the housing 210 can comprise a biocompatible material that has been molded prior to insertion so as to conform to the shape of the portion of the ear canal 102 in which the housing 210 is intended to reside during operation. In certain embodiments, the housing 210 comprises a compliant biocompatible material that is configured to be modified (e.g., by the process of positioning the housing 210 within the ear canal 102) to conform to the shape of the portion of the ear canal 102 in which the housing 110 is intended to reside.

In certain embodiments, the housing 210 does not utilize multiple anchor points to provide mechanical stability to the apparatus 200 within the ear canal 102. In addition, the housing 210 of certain embodiments is positionable within the ear canal 102 so as to be sufficiently discrete such that the presence of the housing 210 within the ear canal 102 cannot be detected by casual observation by others. Certain such embodiments are suitable for use by children recipients.

In certain embodiments, the at least one transducer 220 comprises a microphone configured to convert sound pressure waves 103 within the ear canal 102 to electrical signals. The at least one transducer 220 of certain embodiments comprises a passive microphone (e.g., a microphone which comprises a passive sensing component which utilizes power provided by the passive sensing component for operation; a microphone which does not utilize a battery or other power storage device to provide power for operation). For example, the passive microphone can comprise an electret microphone. For another example, the passive microphone can comprise a piezoelectric microphone comprising a piezoelectric membrane (e.g., polyvinylidenefluoride (PVDF)) configured to generate electrical signals (e.g., output signals 222) in response to forces (e.g., strains and/or stresses) applied to the piezoelectric membrane due to sound pressure waves 103 impinging on the piezoelectric microphone. While the current output amplitude from PVDF membranes can be low, by utilizing backscatter communication as described herein, certain embodiments are able to utilize the current output amplitudes generated by such piezoelectric microphones.

In certain other embodiments, the at least one transducer 220 comprises a microphone which utilizes power stored within the housing 210 (e.g., by a battery, capacitor, or other power storage device). Examples of such microphones compatible with certain embodiments described herein include but are not limited to: optical microphones, condenser microphones, capacitor microphones, electromagnetic induction microphones, and dynamic microphones. In certain embodiments, the at least one transducer 220 comprises a plurality of microphones configured to provide a predetermined total audio frequency response across a range of audio frequencies (e.g., a range up to 8 kHz or 10 kHz) by having each microphone provide a corresponding audio frequency response across a corresponding portion of the range of audible frequencies. For example, the at least one transducer 220 can provide a predetermined total audio frequency response across a range of audio frequencies between 100 Hz and 10 kHz, with a first microphone of the at least one transducer 220 providing an audio frequency response across a first range with a lower bound of 100 Hz and a second microphone of the at least one transducer 220 providing an audio frequency response across a second range with an upper bound of 10 kHz. In certain embodiments, the first range and the second range overlap one another (e.g., the upper bound of the first range is greater than the lower bound of the second range). In certain other embodiments, the first range and the second range are adjacent to one another (e.g., the upper bound of the first range is equal to the lower bound of the second range). In certain other embodiments, the first range and the second range are separated from one another (e.g., the upper bound of the first range is less than the lower bound of the second range).

The foregoing bracketed ranges are typical for normal hearing adults. Children, and possibly some adults, can have even greater audible ranges, e.g., an audible range up to 20 kHz. Thus, certain embodiments described herein operate across a broader range of frequencies. Other embodiments, however, operate across a more narrow range of frequencies. Some recipients of the devices described herein retain so-called residual hearing. For instance, adults often experience high frequency hearing loss before other hearing loss, and for some such recipients, natural hearing in at least part of their residual hearing range is ideal. Thus, the devices for such recipients can be fitted for individuals to exclude at least some their respective residual hearing range. As an individual's residual hearing changes (e.g., diminishes) over time, the device can be refit to operate across a progressively broader range of frequencies.

In certain embodiments, the at least one communication circuit 230 is configured to modulate the at least one resonance frequency in response to the output signals 222 from the at least one transducer 220 using various modulation schemes. Examples of modulation schemes for modulating the at least one resonance frequency include but are not limited to: frequency modulation, amplitude modulation, phase modulation, and digital modulation. As described herein, modulating the at least one resonance frequency can correspondingly modulate the second electromagnetic signals 304 radiated from the apparatus 200 (e.g., the backscattered portion of the first electromagnetic signals 302 from the implantable device) so as to encode information indicative of the detected sound (e.g., sound data) onto the second electromagnetic signals 304. In certain embodiments, the modulations of the at least one resonance frequency are at a modulation frequency (e.g., less than a base frequency of the first electromagnetic signals 302; at an audio frequency; in a range between 8 kHz and 10 kHz; in a range between 10 kHz and 100 kHz).

Figure 3A:
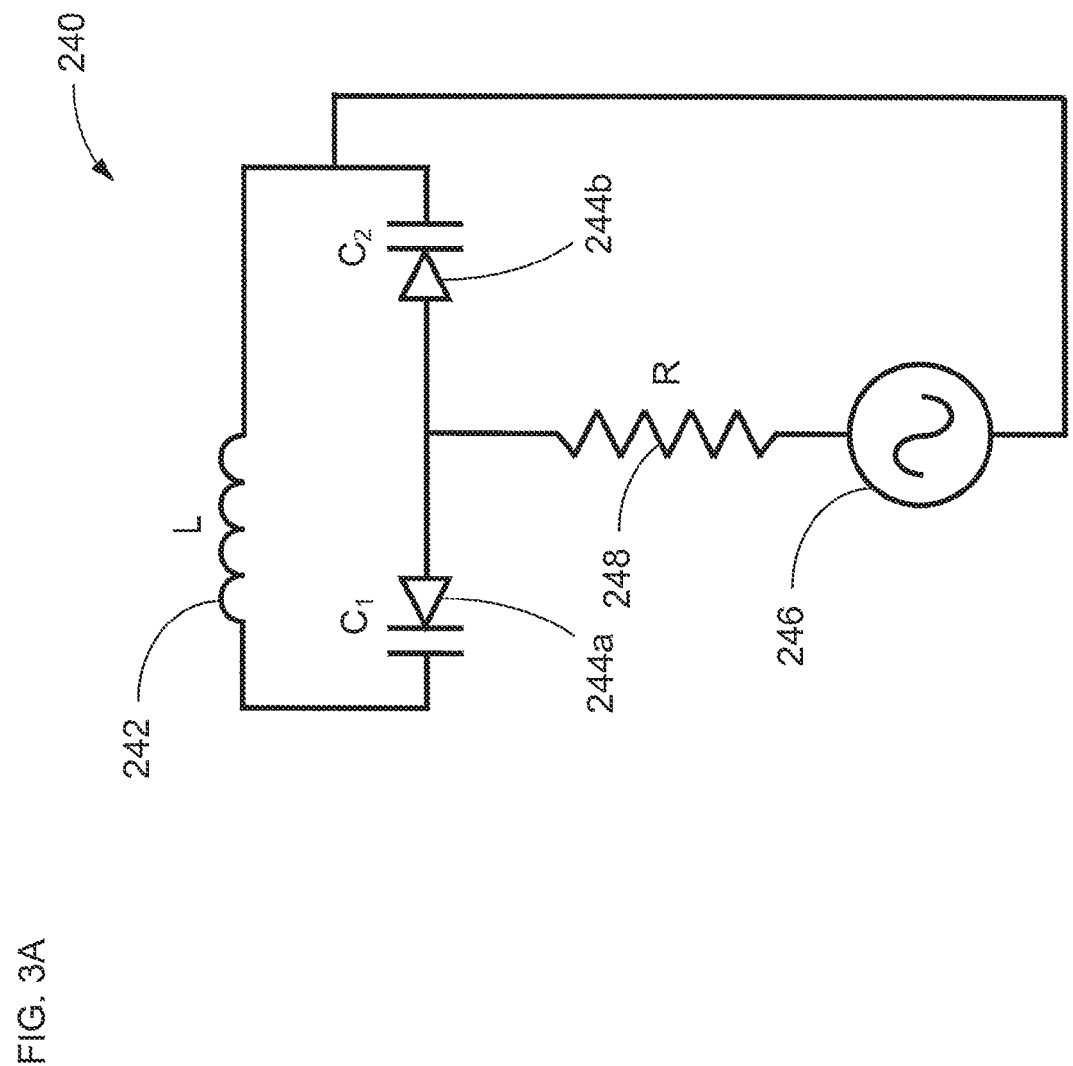
FIG. 3A schematically illustrates an example antenna circuit compatible with certain embodiments described herein.

In certain embodiments, the at least one communication circuit 230 comprises at least one antenna circuit 240 configured to wirelessly receive at least one signal from a device (e.g., implantable excitation device 120; apparatus 300) implanted in the recipient. FIG. 3A schematically illustrates an example antenna circuit 240 compatible with certain embodiments described herein. The antenna circuit 240 can comprise one or more circuit elements 242 (e.g., inductors; variable inductors) providing an inductance L and one or more circuit elements 244 (e.g., varactor diodes; capacitors; variable capacitors) providing a capacitance C. The antenna circuit 240 of certain embodiments has an impedance Z and a resonance frequency $f_0$ (e.g., $f_0 = 1/2\pi\sqrt{LC}$, with $f_0$ in units of hertz, L in units of henrys, and C in units of farads). Both the impedance Z and the resonance frequency $f_0$ of the antenna circuit 240 are dependent on the inductance L and the capacitance C. In certain embodiments, the at least one communication circuit 230 is configured to modulate the at least one impedance Z and/or the at least one resonance frequency $f_0$ of the at least one antenna circuit 240 by modulating at least one of the inductance L and the capacitance C.

For example, the example antenna circuit 240 of FIG. 3A comprises circuit element 242 having an inductance L, two circuit elements 244a, 244b (e.g., two back-to-back varactor diodes) each having a corresponding variable capacitance $C_1$, $C_2$, and an isolating series input resistor 248 having a resistance R. Each of the two variable capacitances $C_1$, $C_2$ is responsive, at least in part, to an input voltage signal 246 (e.g., the output signal 222 received from the at least one transducer 220), such that the antenna circuit 240 has a total capacitance C that can be modulated in response to the input voltage signal 246, thereby modulating the resonance frequency $f_0$ (e.g., tuning and detuning the antenna circuit 240).

In certain embodiments, the at least one communication circuit 230 comprises a plurality of communication circuits 230 (e.g., a plurality of antenna circuits 240), each of which has a corresponding resonance frequency $f_0$ (e.g., different from one another). The plurality of communication circuits 230 can be configured to receive the output signals 222 from the at least one transducer 220 and to modulate, in response to the output signals 222 from the at least one transducer 220, one or more of the resonance frequencies corresponding to the plurality of communication circuits 230.

The at least one antenna circuit 240 of certain embodiments comprises one or more antennas, examples of which include but are not limited to: dipole antennas, monopole antennas, loop antennas, spiral antennas, patch antennas, slot antennas, helical antennas, coil antennas, and phased arrays of antennas. In certain embodiments, the at least one antenna circuit 240 has a radiation pattern (e.g., a spatial distribution characterizing the electromagnetic field generated by the antenna circuit) that facilitates wireless communication with the implantable device. For example, the radiation pattern can be rotationally symmetric (e.g., omnidirectional) about an axis direction (e.g., a direction parallel to a longitudinal axis of the housing 210). For another example, the at least one antenna circuit 240 can comprise a directional antenna (e.g., an antenna having a radiation pattern with a lobe extending along a direction generally towards a location of an antenna of the implanted device). For another example, the at least one antenna circuit 240 can comprise a plurality of antenna circuits 240, each of which has a corresponding non-isotropic radiation pattern with a corresponding symmetry axis, and the symmetry axes are non-parallel (e.g., perpendicular) to one another. The plurality of antenna circuits 240 can be positioned and oriented relative to one another to provide a total radiation pattern that facilitates wireless communication with the implantable device, regardless of the direction (e.g., approximating an isotropic radiation pattern).

Figure 3B:
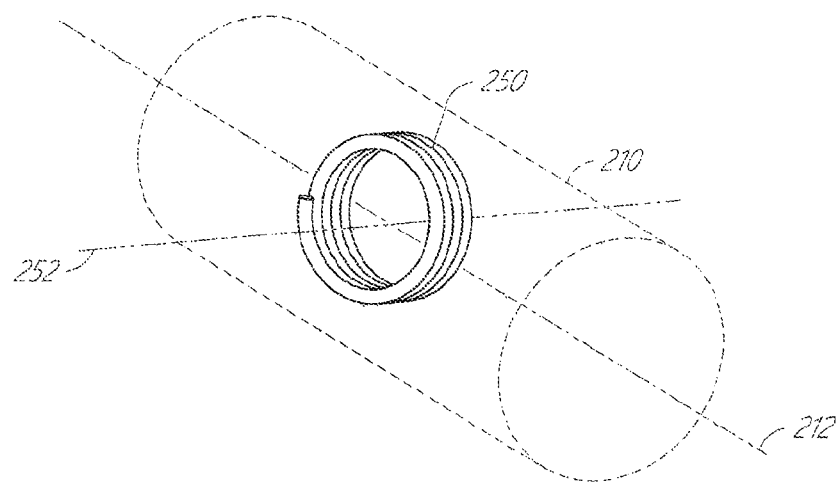
FIGS. 3B-3E schematically illustrate example coil antennas in accordance with certain embodiments described herein.
Figure 3C:
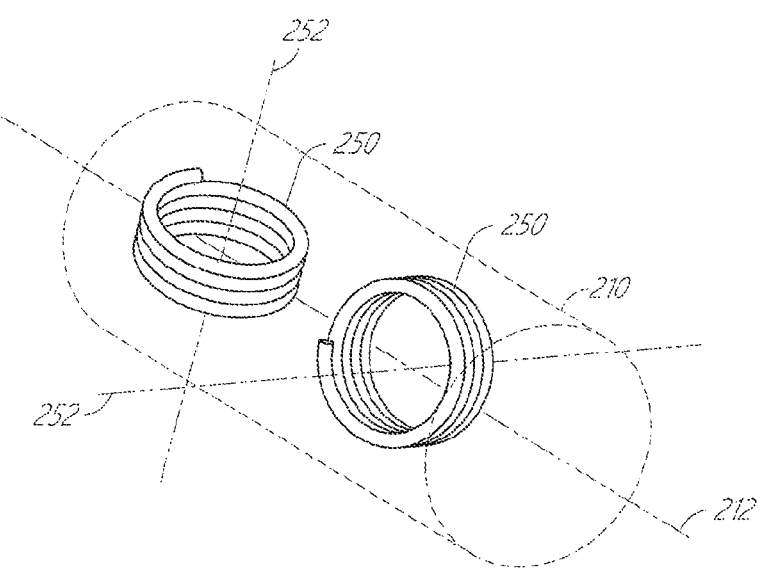
Figure 3D:
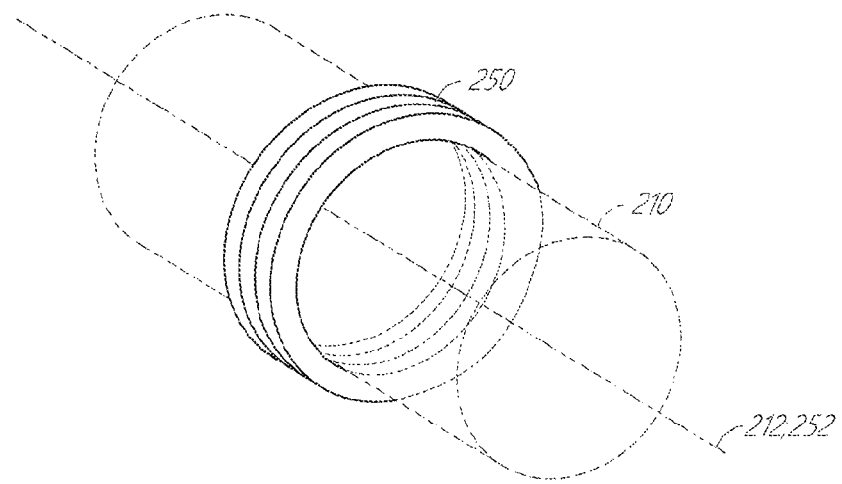
Figure 3E:
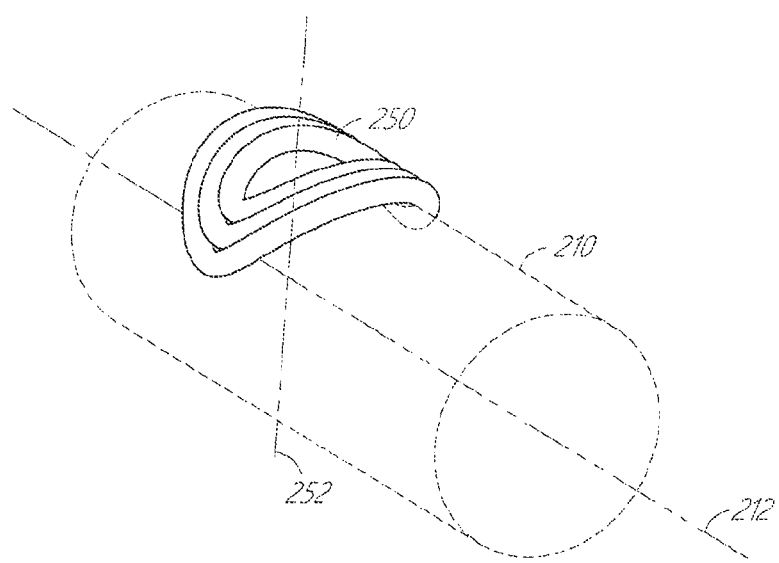

In certain embodiments, the at least one antenna circuit 240 comprises one or more coil antennas 250 (e.g., comprising one or more circuit elements 242). FIGS. 3B-3E schematically illustrate example coil antennas 250 in accordance with certain embodiments described herein. The example coil antenna 250 of FIG. 3B has a plurality of coils and is inside the housing 210. The axis 252 of the coil antenna 250 of FIG. 3B is generally perpendicular to the coils and to a longitudinal axis 212 of the housing 210. The two example coil antennas 250 of FIG. 3C each has a plurality of coils and is inside the housing 210. The axis 252 of each coil antenna 250 of FIG. 3C is generally perpendicular to the coils of the coil antenna 250, to the axis 252 of the other coil antenna 250, and to the longitudinal axis 212 of the housing 210. The example coil antenna 250 of FIG. 3D has a plurality of coils that are wrapped completely around the longitudinal axis 212 of the housing 210, with the axis 252 of the coil antenna 250 generally perpendicular to the coils and generally parallel to the longitudinal axis 212 of the housing 210. While FIG. 3D shows an embodiment in which the coil antenna 250 is wrapped around and outside an outer perimeter of the housing 210, in certain other embodiments, the coil antenna 250 is wholly within the housing 210 (e.g., embedded within a wall of the housing 210; positioned within an inner surface of the housing 210). The example coil antenna 250 of FIG. 3E has a plurality of coils that extend partially along the outer perimeter of the housing 210, with the axis 252 of the coil antenna 250 generally perpendicular to the coils and generally perpendicular to the longitudinal axis 212 of the housing 210. While FIG. 3E shows an embodiment in which the coil antenna 250 is outside the outer perimeter of the housing 210, in certain other embodiments, the coil antenna 250 is wholly within the housing 210 (e.g., embedded within a wall of the housing 210; positioned within an inner surface of the housing 210).

Various other configurations of coil antennas 250 in accordance with certain embodiments described herein include combinations of two or more of the coil antennas 250 of FIGS. 3B-3E, with the axes 252 of the coil antennas 250 generally perpendicular to one another, generally parallel to one another, or having other angles between one another. These various other configurations of coil antennas 250 can also have one or more axes 252 that are generally perpendicular to the longitudinal axis 212 of the housing 210, generally parallel to the longitudinal axis 212, or having other angles between the axes 252 and the longitudinal axis 212. In certain embodiments in which the at least one antenna circuit 240 comprises two or more coil antennas 250 having axes 252 generally perpendicular to one another, the coupling of the at least one antenna circuit 240 with the carrier signal from the implantable excitation device 120 is insensitive to rotation of the apparatus 200 about the longitudinal axis 212 of the housing 210, and operation of the apparatus 200 is insensitive to rotation of the apparatus 200 about the longitudinal axis 212.

Figure 3F:
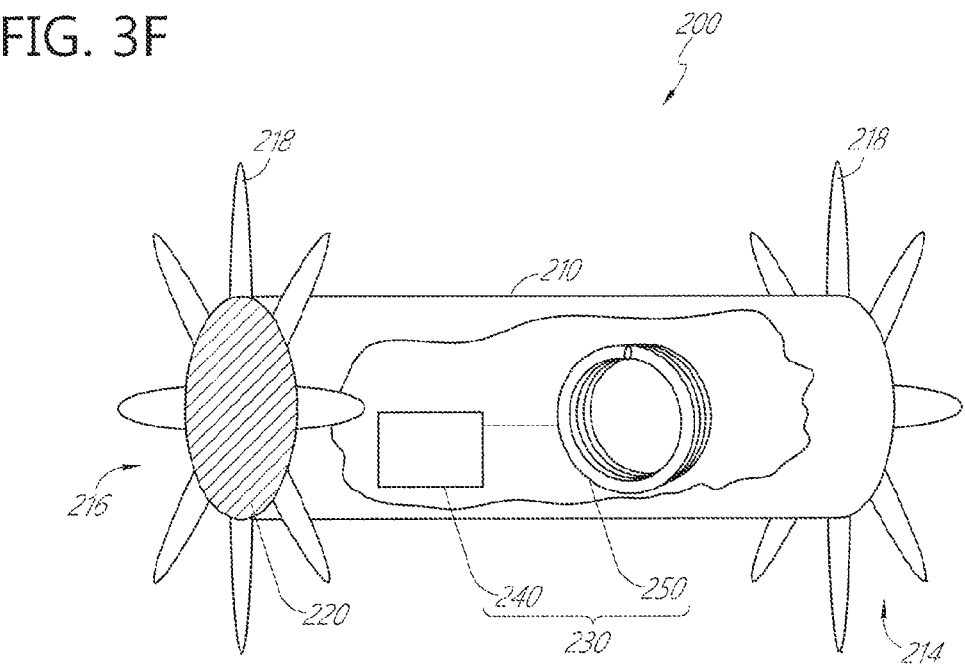
FIGS. 3F-3G schematically illustrate two views of an example housing, transducer, and communication circuit compatible with certain embodiments described herein.
Figure 3G:
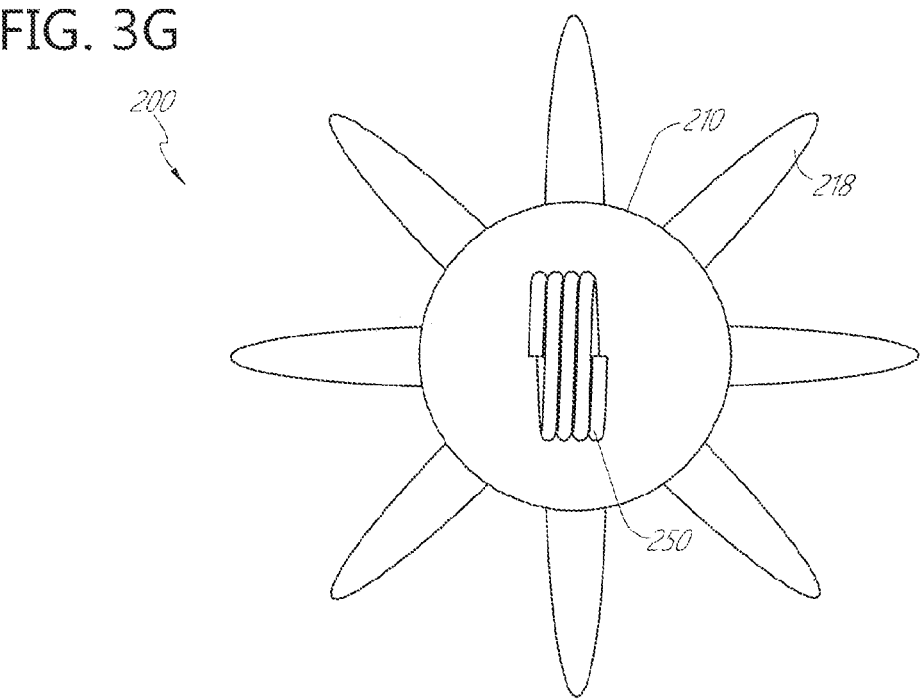

FIGS. 3F-3G schematically illustrate two views of an example housing 210, transducer 220, and communication circuit 230 compatible with certain embodiments described herein. FIG. 3F shows a perspective view of the housing 210 with a cut-away portion showing the communication circuit 230 comprising antenna circuitry 240 that comprises a coil antenna 250 within the housing 210. FIG. 3G shows a view into an open first end 214 of the housing 210 and the coil antenna 250 within the housing 210.

The housing 210 of FIGS. 3F-3G has a tubular shape and has a first end 214 and a second end 216, each of the first end 214 and the second end 216 comprising one or more protrusions 218 extending outwardly away from a longitudinal axis 212 of the housing 210. The protrusions 218 (e.g., fingers; ribs; rings; or similar structures) are configured to contact an inner surface of the ear canal 102 of the recipient and to keep the apparatus 200 in place and aligned with the ear canal 102 (e.g., in alignment with the antennas of the apparatus 300). In certain other embodiments, the housing 210 comprises a single set of protrusions 218 (e.g., positioned at one end of the housing 210 or the other; positioned between the two ends of the housing 210) and configured to contact the inner surface of the ear canal 102 of the recipient to keep the apparatus 200 in place, although certain such embodiments do not keep the apparatus 200 aligned with the ear canal 102 (e.g., not in alignment with the antennas of the apparatus 300). The protrusions 218 of certain embodiments are configured to allow sound to propagate past the apparatus 200 (e.g., through spaces between adjacent protrusions 218) to the tympanic membrane 104 of the recipient, thereby allowing the recipient to utilize residual hearing capabilities.

The transducer 220 schematically illustrated by FIG. 3F comprises a piezoelectric membrane configured to generate electrical signals (e.g., output signals 222) in response to forces (e.g., strains and/or stresses) applied to the piezoelectric membrane due to sound pressure waves 103 impinging on the piezoelectric membrane. In certain embodiments, the housing 210 is positionable such that the first end 214 of the housing 210 faces away from the tympanic membrane 104 and the second end 216 of the housing 210 faces towards the tympanic membrane 104. In certain other embodiments, the housing 210 is positionable such that the first end 214 of the housing 210 faces towards the tympanic membrane 104 and the second end 216 of the housing 210 faces away from the tympanic membrane 104. As schematically illustrated by FIG. 3F, the first end 214 of the housing 210 is configured to allow sound to enter the housing 210 (e.g., the first end 214 is open and faces away from the tympanic membrane 104) and the piezoelectric membrane is positioned at the second end 216 of the housing 210 (e.g., the second end 216 is closed by the piezoelectric membrane and faces towards the tympanic membrane 104).

The communication circuit 230 of FIG. 3F is configured to receive the electrical signals from the transducer 220 and comprises at least one antenna circuit 240 and a coil antenna 250. The coil antenna 250 of FIGS. 3F-3G is oriented with its axis 252 generally perpendicular to the longitudinal axis 212 of the housing 210.

As described herein, by modulating the at least one resonance frequency, certain embodiments described herein are configured to interact with the at least one signal wirelessly received from the implanted device (e.g., implantable excitation device 120; apparatus 300) to modulate signals radiated from the apparatus 200. In certain embodiments in which the modulated signals radiated from the apparatus 200 comprise portions of the at least one signal reflected back or echoed back to the implanted device, the apparatus 200 can be referred to as a "passive backscatter transmitter" which transmits information (e.g., via backscatter communications) indicative of the sound within the ear canal 102 to the implanted device.

In certain embodiments in which the at least one antenna circuit 240 comprises a straight-style (e.g., rod-style) antenna (e.g., dipole antenna; monopole antenna), the length of the antenna is selected to correspond to the carrier frequency with which the antenna interacts, such that the length is inversely proportional to the corresponding carrier frequency. Depending on the implementation, certain embodiments comprising straight antennas utilize calculable carrier frequencies. For example, a length of 3 centimeters can be appropriate for use with a carrier frequency of 2.4 GHz, a length of 1.5 centimeters can be appropriate for use with a carrier frequency of 4.8 GHz, a length of 0.75 centimeter can be appropriate for use with a carrier frequency of 9.6 GHz, and so on.

In certain embodiments, the apparatus 200 comprises other features and functionalities. The apparatus 200 of certain embodiments comprises a microcontroller (e.g., a processor integrated circuit) configured to monitor performance of and/or to provide signals to various components of the apparatus 200 (e.g., to adjust performance parameters of the at least one transducer 220, the at least one communication circuit 230, and/or one or more other components of the apparatus 200). In certain such embodiments, the microcontroller is configured to wirelessly receive control signals from an external device (e.g., control signals encoded onto the at least one signal wirelessly received from the implantable device). The apparatus 200 of certain embodiments comprises power storage circuitry (e.g., one or more batteries, rechargeable batteries, non-rechargeable batteries, capacitors, or other power storage devices) configured to store power and to provide the power to other components of the apparatus 200. The apparatus 200 of certain embodiments comprises power reception circuitry configured to wirelessly receive power and to provide the power to the power storage circuitry or to other components of the apparatus 200. Examples of power reception circuitry can include, but are not limited to: a coil configured to move within a magnetic field (e.g., a dynamic microphone coil of the apparatus 200); a piezoelectric element (e.g., PVDF membrane of a piezoelectric microphone of the apparatus 200) responding to frequencies outside of the human audible range; circuitry configured to wirelessly receive electrical power from a dedicated source (e.g., a pillow charger); circuitry configured to extract electrical power from signals wirelessly received by the apparatus 200 (e.g., the at least one signal from the implanted device); thermoelectric, piezoelectric, or radio-frequency (RF) transducers configured to harvest power from energy received from the ambient environment of the apparatus 200 (e.g., thermal energy; kinetic energy; RF energy) and to convert the harvested power into electrical power.

In certain embodiments, by being configured to be positioned within the ear canal 102 of the recipient, the apparatus 200 is configured to utilize the directionality naturally provided by the outer ear 101 and the ear canal 102. For example, the apparatus 200 can provide the user with information regarding the direction from which the detected sound was received, instead of utilizing power-hungry signal processing, as is otherwise used with devices using microphones that are positioned outside the ear canal 102 (e.g., on the ear; off the ear; implanted under the skin behind the ear). In certain embodiments, by being configured to be positioned within the ear canal 102 of the recipient, the apparatus 200 is configured to operate without performance degradation and/or challenges involved with detecting sound transmitted through skin tissue, as is otherwise used with devices using implanted (e.g., subcutaneous) microphones. In addition, by being positioned within the ear canal 102, the apparatus 200 of certain embodiments is shielded by the recipient's body tissue from electromagnetic interference at higher operating frequencies, such that the influence of electromagnetic interference is lessened.

In certain embodiments, the apparatus 200 does not introduce latency issues to the recipient's perception of sound (e.g., introduces little or no latency to the operation of recipient's auditory system; introduces an amount of latency that is tolerable by the recipient; introduces an amount of latency that does not appreciably interfere with the recipient's determination of the direction from which sound is coming from). For example, any latency introduced by the apparatus 200 can be less than 25 milliseconds.

Figure 4:
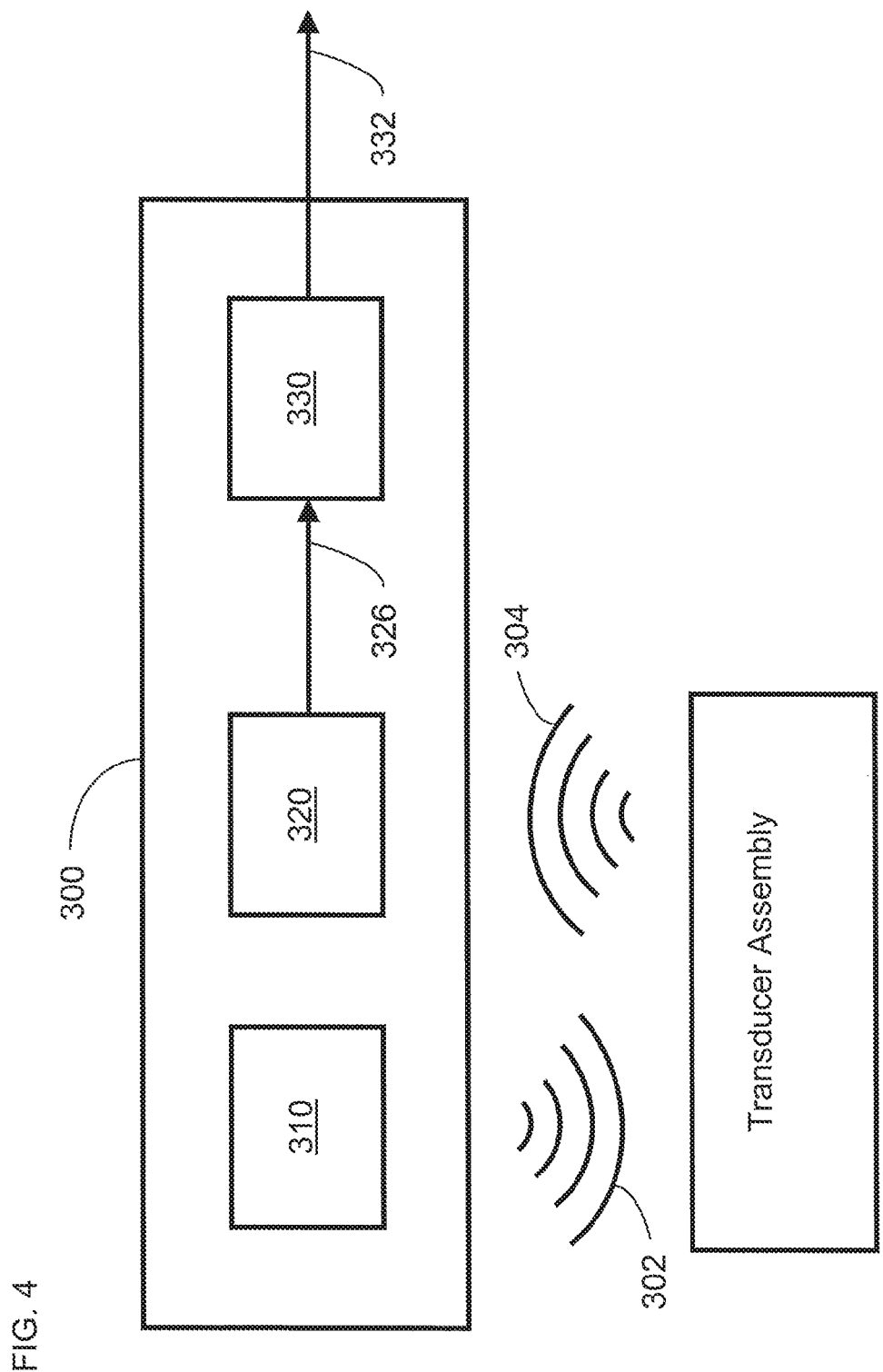
FIG. 4 schematically illustrates an example apparatus (e.g., an implantable excitation device) compatible with certain embodiments described herein.

FIG. 4 schematically illustrates an example apparatus 300 (e.g., an implantable excitation device 120; a cochlear implant; a direct acoustic cochlear implant; a bone conduction auditory prosthesis; a middle ear auditory prosthesis; an auditory brainstem implant; any combination thereof) compatible with certain embodiments described herein. The apparatus 300 comprises at least one transmission circuit 310 configured to wirelessly transmit first electromagnetic signals 302 to a transducer assembly (e.g., electroacoustic transducer; apparatus 200 comprising at least one transducer 220; ITEC microphone 110) positioned within an ear canal 102 of a recipient. The apparatus 300 further comprises at least one detection circuit 320 configured to detect second electromagnetic signals 304 radiated from the transducer assembly, the second electromagnetic signals comprising a portion of the first electromagnetic signals reflected from the transducer assembly. The apparatus 300 further comprises at least one excitation assembly 330 configured to generate excitation signals 332 in response to the second electromagnetic signals 304. For example, the second electromagnetic signals can comprise modulations that define data indicative of sound received by the transducer assembly, the at least one detection circuit can be configured to detect said modulations, and the at least one excitation assembly can be configured to generate excitation signals in response to said detected modulations.

In response to the first electromagnetic signals 302, the second electromagnetic signals 304 are radiated from the transducer assembly. For example, the second electromagnetic signals 304 can be a portion of the first electromagnetic signals 302 reflected from the transducer assembly (e.g., apparatus 200 comprising at least one transducer 220; ITEC microphone 110) to the apparatus 300 (e.g., backscattered). As described herein, modulations imparted to the second electromagnetic signals 304 by the transducer assembly are indicative of the sound received by the transducer assembly. In other words, in many embodiments, second electromagnetic signals can include embedded sound data (e.g., embodied within the modulations).

Figure 5A:
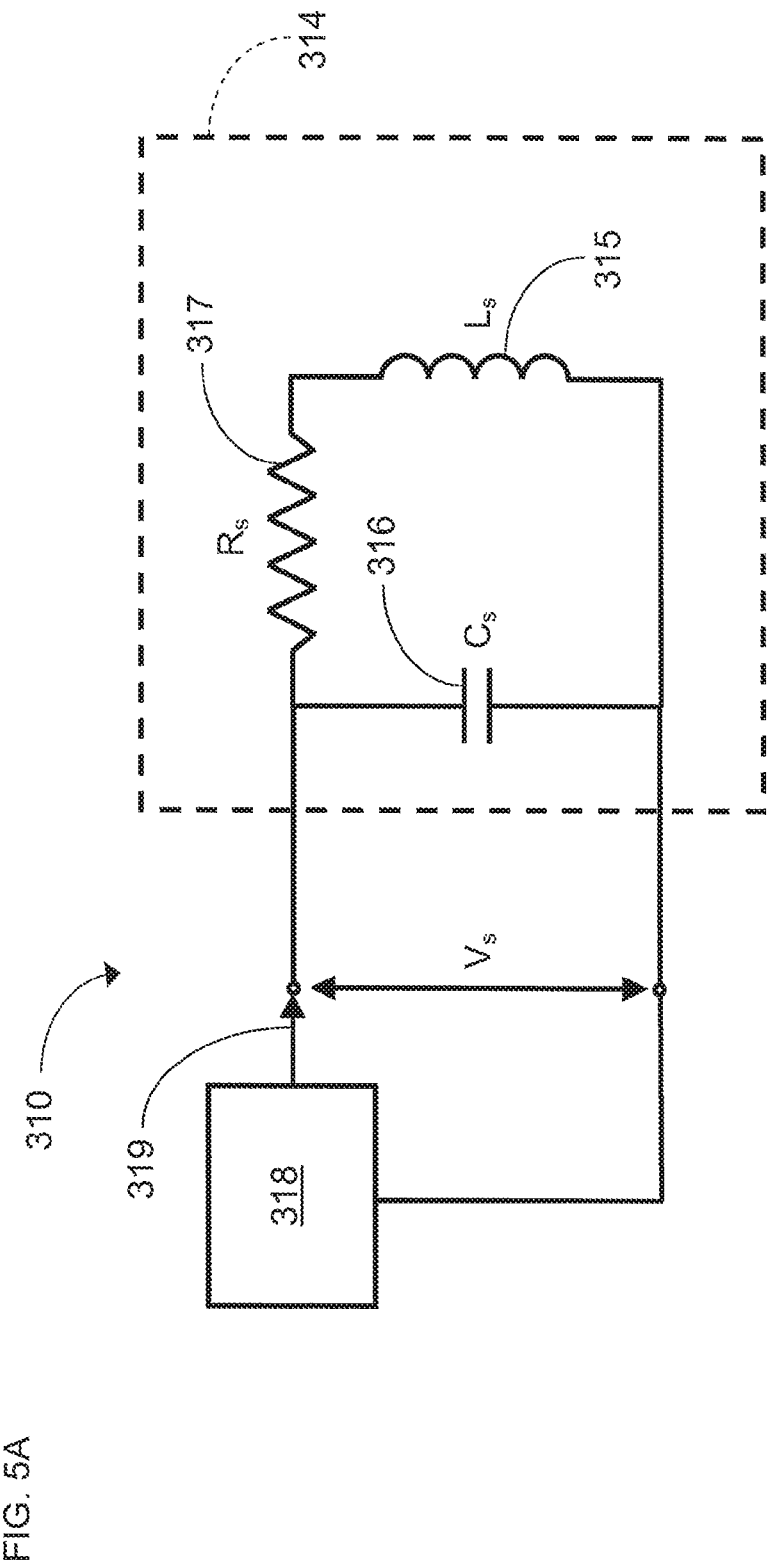
FIG. 5A schematically illustrates an example transmission circuit in accordance with certain embodiments described herein.

FIG. 5A schematically illustrates an example transmission circuit 310 in accordance with certain embodiments described herein. In certain embodiments, the at least one transmission circuit 310 comprises at least one transmission antenna 314 and transmission circuitry 318 configured to provide an input signal 319 to the at least one transmission antenna 314. The transmission antenna 314 can comprise at least one inductor 315 providing an inductance $L_s$, at least one capacitor 316 providing a capacitance $C_s$, and at least one resistor 317 providing a resistance $R_s$. The transmission antenna 314 can be considered to be an "LC" or "RLC" resonance circuit which receives the input signal 319 (e.g., an input voltage $V_s$). The transmission circuitry 318 can comprise an alternating-current ("AC") power supply configured to generate the input signal 319 having a predetermined frequency. In response to the input signal 319, the transmission antenna 314 can generate and wirelessly transmit the first electromagnetic signals 302, at least a portion of which is wirelessly transmitted to the transducer assembly positioned within the ear canal 102 of the recipient.

In certain embodiments, the first electromagnetic signals 302 comprise continuous-wave ("CW") electromagnetic signals (e.g., having a constant amplitude and a constant base frequency) and the transmission circuit 310 is configured to transmit the first electromagnetic signals 302 substantially continuously while the transmission circuit 310 is powered. In certain embodiments, the first electromagnetic signals 302 has a predetermined base frequency and is configured to interact with a portion of the transducer assembly (e.g., the at least one communication circuit 230 of the apparatus 200). The predetermined base frequency and intensity of the first electromagnetic signals 302 can be configured to provide an intensity of the first electromagnetic signals 302 at the transducer assembly sufficient for operation as described herein, while not generating heat (due to absorption of the first electromagnetic signals 302 by tissue between the apparatus 300 and the apparatus 200) that causes significant damage or discomfort to the recipient. For example, the first electromagnetic signals 302 can have a base frequency in a range between 100 kHz and 10 MHz (e.g., 124 kHz; 125 kHz; 135 kHz; other low-frequency radio bands), in a range between 10 MHz and 100 MHz (e.g., 13.56 MHz; other high-frequency radio bands), between 100 MHz and 1 GHz, or in a range between 100 MHz and 5 GHz (e.g., 2.45 GHz; other ultra-high radio bands). Other ranges of frequencies are also compatible with certain embodiments described herein.

In certain embodiments, the transmission circuit 310 is configured to encode the first electromagnetic signals 302 with control signals or other information to be transmitted from the apparatus 300 to the apparatus 200. For example, the transmission circuit 310 can be configured to controllably turn off and on transmission of the first electromagnetic signals 302 with varying durations during operation (e.g., with the varying durations used to convey control signals or other information). For another example, the first electromagnetic signals 302 can comprise carrier signals having a predetermined base frequency on which control signals or other information is encoded (e.g., by having one or more of an amplitude, a phase, and the base frequency of the carrier signals modulated by the transmission circuit 310 at a modulation frequency lower than the base frequency) to transmit the control signals or other information from the apparatus 300 to the transducer assembly (e.g., ITEC microphone 110; apparatus 200). In certain embodiments, the first electromagnetic signals 302 transmit power to the transducer assembly (e.g., the apparatus 200). The transducer assembly can include circuitry configured to decode the received carrier signals to extract the control signals or other information and/or to extract electrical power from the received carrier signals.

Figure 5C:
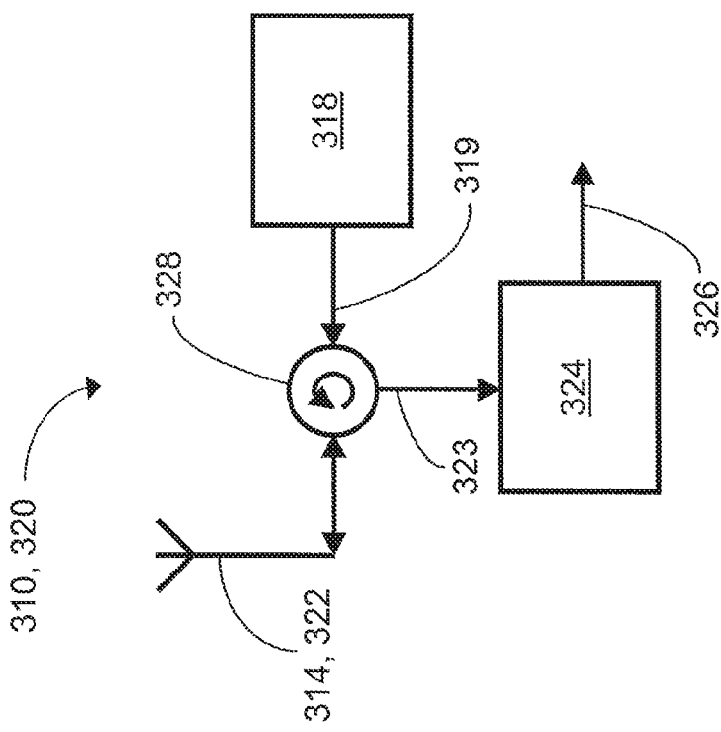
FIG. 5C schematically illustrates an example transmission circuit and detection circuit having at least one antenna in common with one another in accordance with certain embodiments described herein.
Figure 5B:
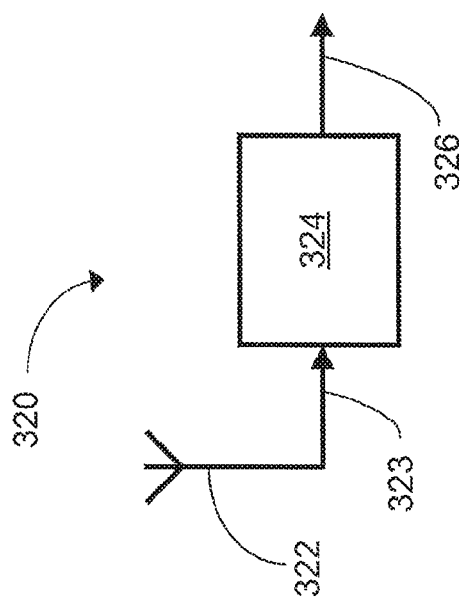
FIG. 5B schematically illustrates an example detection circuit in accordance with certain embodiments described herein.

FIG. 5B schematically illustrates an example detection circuit 320 in accordance with certain embodiments described herein. In certain embodiments, the at least one detection circuit 320 comprises at least one detection antenna 322 and detection circuitry 324 configured to monitor and/or detect modulation of the second electromagnetic signals 304 (e.g., the second electromagnetic signals comprise a portion of the first electromagnetic signals 302 reflected from the transducer assembly and can also comprise modulations of the portion reflected) and to generate output signals 326 in response to the detected modulation.

The detection antenna 322 can comprise at least one inductor, at least one capacitor, and at least one resistor, and can be considered to be an "LC" or "RLC" resonance circuit configured to receive at least a portion of the second electromagnetic signals 304 radiated from the transducer assembly and to generate detected signals 323 which are inputted from the detection antenna 322 to the detection circuitry 324. In certain embodiments, the detection circuitry 324 comprises one or more filters, demodulators, and decoders configured to analyze the detected signals 323 to detect a modulation of the second electromagnetic signals 322, to generate output signals 326 in response to the detected modulation, and to provide the output signals 326 to the at least one excitation assembly 330. The output signals 326 can be indicative of the sound received by the transducer assembly (e.g., apparatus 200 comprising at least one transducer 220; ITEC microphone 110).

In certain embodiments, the at least one transmission antenna 314 and the at least one detection antenna 322 are separate from one another, while in certain other embodiments, the at least one transmission antenna 314 and the at least one detection antenna 322 have at least one antenna in common with one another. For example, FIG. 5C schematically illustrates an example transmission circuit 310 and detection circuit 320 having at least one antenna 314, 322 in common with one another in accordance with certain embodiments described herein. The common antenna 314, 322 is in electrical communication with a coupler 328 (e.g., circulator) which is in electrical communication with the transmission circuitry 318 and configured to receive the input signal 319 from the transmission circuitry 318 and to provide the input signal 319 to the common antenna 314, 322. The coupler 328 is also in electrical communication with the detection circuitry 324 and configured to receive the detected signal 323 from the common antenna 314, 322 and to provide the detected signal 323 to the detection circuitry 324. In certain such embodiments, the coupler 328 is configured to provide signal isolation between the transmission circuitry 318 and the detection circuitry 324 such that the detection circuitry 324 is not unduly affected by cross-talk (e.g., a portion of the input signal 319 being inputted to the detection circuitry 324) with the transmission circuit 310.

Each of the at least one transmission antenna 314 and the at least one detection antenna 322 of certain embodiments comprises one or more antennas, examples of which include but are not limited to: dipole antennas, monopole antennas, loop antennas, spiral antennas, patch antennas, slot antennas, helical antennas, coil antennas, and phased arrays of antennas. In certain embodiments, the one or more antennas (e.g., the at least one transmission antenna 314 and the at least one detection antenna 322) has a radiation pattern that facilitates wireless communication with the transducer assembly. For example, the radiation pattern can be rotationally symmetric (e.g., omnidirectional) about an axis direction. For another example, the at least one antenna can comprise a directional antenna (e.g., an antenna having a radiation pattern with a lobe extending along a direction generally towards a location of an antenna of the transducer assembly). For another example, the at least one antenna can comprise a plurality of antennas, each of which has a corresponding non-isotropic radiation pattern with a corresponding symmetry axis, and the symmetry axes are non-parallel (e.g., perpendicular) to one another. The plurality of antennas can be positioned and oriented relative to one another to provide a total radiation pattern that facilitates wireless communication with the transducer assembly, regardless of the direction (e.g., approximating an isotropic radiation pattern).

In certain embodiments in which one or both of the at least one transmission antenna 314 and the at least one detection antenna 322 comprises a straight-style (e.g., rod-style) antenna (e.g., dipole antenna; monopole antenna), the length of the antenna is selected to correspond to the carrier frequency, such that the length is inversely proportional to the corresponding carrier frequency. Depending on the implementation, certain embodiments comprising straight antennas utilize calculable carrier frequencies. For example, a length of 3 centimeters can be appropriate for use with a carrier frequency of 2.4 GHz, a length of 1.5 centimeters can be appropriate for use with a carrier frequency of 4.8 GHz, a length of 0.75 centimeter can be appropriate for use with a carrier frequency of 9.6 GHz, and so on.

In certain embodiments, the one or more antennas comprise a plurality of coils positioned around the ear canal 102 (e.g., oriented 90 degrees from one another) such that a magnetic field from the apparatus 300 to the transducer assembly (e.g., apparatus 200; ITEC microphone 110) is substantially homogeneous, thereby providing robustness with regard to placement of the transducer assembly within the ear canal 102, utilizing low amounts of energy for operation, and/or utilizing a distance between the one or more antennas and the transducer assembly of several millimeters.

In certain embodiments, the one or more antennas of the apparatus 300 (e.g., the at least one transmission antenna 314 and the at least one detection antenna 322) are configured to be positioned to be substantially adjacent to the transducer assembly (e.g., apparatus 200 comprising at least one transducer 220; ITEC microphone 110) positioned within the ear canal 102 of the recipient. For example, the one or more antennas can be configured to be positioned within the middle ear cavity of the recipient within a distance from the transducer assembly (e.g., within 3 millimeters; within 5 millimeters; within 10 millimeters) with intervening tissue (e.g., ear canal wall tissue; other tissue) between the one or more antennas and the transducer assembly. In certain embodiments, the apparatus 300 and the apparatus 200 are tunable to leverage the close spacing of the one or more antennas of the apparatus and the one or more antennas of the apparatus 200 such that the level of power utilization is sufficient for operation as described herein, while not generating heat (due to absorption of the first electromagnetic signals 302 by tissue between the apparatus 300 and the apparatus 200) that causes significant damage or discomfort to the recipient.

Figure 5D:
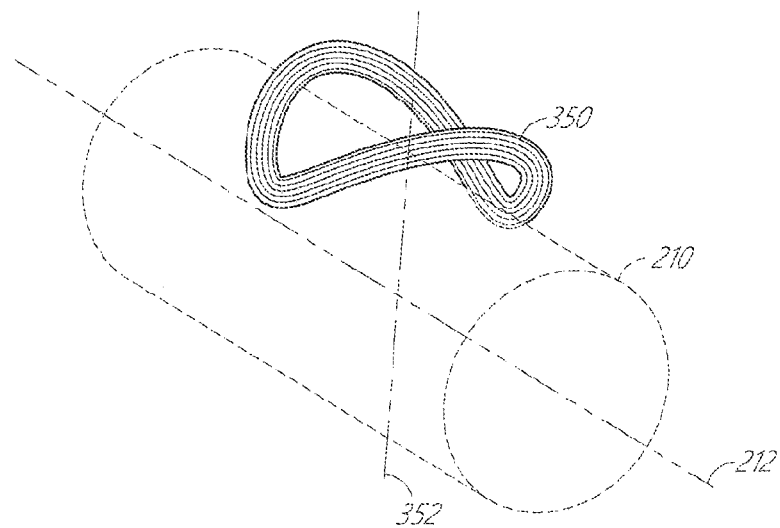
FIGS. 5D-5E schematically illustrate example coil antennas in accordance with certain embodiments described herein.
Figure 5E:
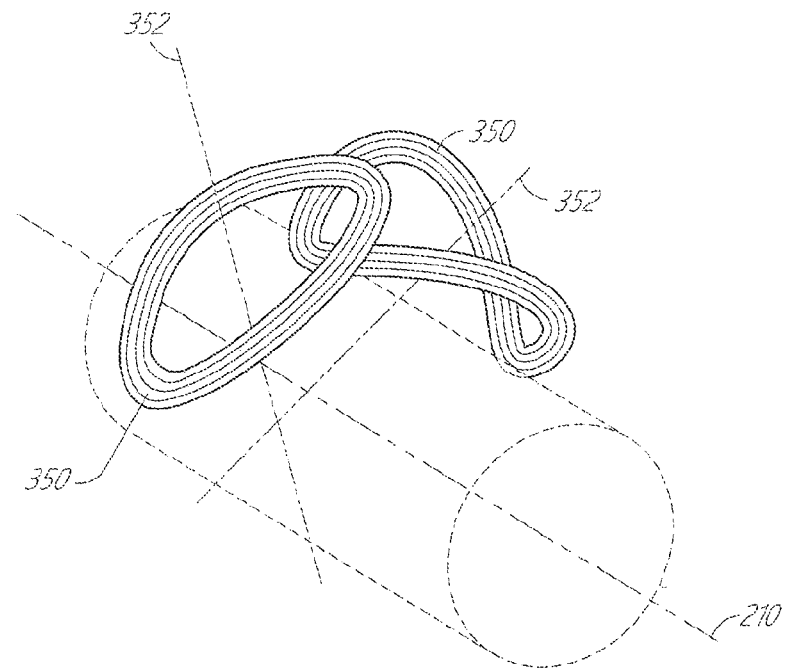

In certain embodiments, the one or more antennas of the apparatus 300 (e.g., the at least one transmission antenna 314 and the at least one detection antenna 322) comprises one or more coil antennas 350. FIGS. 5D-5E schematically illustrate example coil antennas 350 in accordance with certain embodiments described herein. The example coil antenna 350 of FIG. 5D has a plurality of coils and is positionable to extend at least partially around the ear canal 102 of the recipient (e.g., at least partially around the housing 210 of the apparatus 200). The axis 352 of the coil antenna 350 of FIG. 5D is generally perpendicular to the coils and to a longitudinal axis of the ear canal 102 (e.g., generally perpendicular to the longitudinal axis 212 of the housing 210). Each of the two example coil antennas 350 of FIG. 5E has a plurality of coils and is positionable to extend at least partially around the ear canal 102 of the recipient. In some embodiments, the axis 352 of each coil antenna 350 of FIG. 5E is generally perpendicular to the other of the coil antenna 350 and to the longitudinal axis of the ear canal 102. In other embodiments, the relationship between these axes is different. The two coil antennas 350 of FIG. 5E partially overlap one another and extend over a larger range of azimuthal angles around the longitudinal axis of the ear canal 102 than does the single coil antenna 350 of FIG. 5D. For example, the two coil antennas 350 of FIG. 5E can extend about half way (e.g., 180 degrees) around the ear canal 102, while each of the two coil antennas 350 individually only extends about one-fourth (e.g., 90 degrees) to one-third (e.g., 120 degrees) around the ear canal 102. In certain such embodiments, at least one of the two or more coil antennas 350 that extend at least partially around the ear canal 102 will have a suitably strong coupling with the at least one antenna circuit 240 of the apparatus 200. During operation of the apparatus 300, the apparatus 300 utilizes the one of the two or more coil antennas 350 which has the strongest coupling with the at least one antenna circuit 240 of the apparatus 200. By selecting to use the coil antenna 350 with the strongest coupling with the at least one antenna circuit 240 of the apparatus 200, certain embodiments are advantageously operated with less sensitivity to orientation of the apparatus 200 than is an apparatus 300 with a single coil antenna 350 (e.g., as schematically illustrated by FIG. 5D). The example coil antennas 350 of FIGS. 5D-5E can be utilized with one or more of the example coil antennas 250 of FIGS. 3B-3E, or combinations thereof, in accordance with certain embodiments described herein.

In certain embodiments, the apparatus 300 comprises an implantable auditory prosthesis and the at least one excitation assembly 330 comprises an implantable excitation assembly 330 of the implantable auditory prosthesis. The at least one excitation assembly 330 can be configured to receive the output signals 326 from the detection circuitry 324 and configured to generate the excitation signals 332 in response to the output signals 326, the excitation signals 332 comprising signals indicative of the sound received by the transducer assembly (e.g., apparatus 200 comprising at least one transducer 220; ITEC microphone 110) and configured to be provided to at least a portion of the recipient's auditory system (e.g., to stimulate the perception of sound by the recipient). For example, the apparatus 300 can function similarly to a traditional cochlear implant, with the at least one excitation assembly 330 comprising an electrode array implanted in the cochlea 140 to be in operational communication with the auditory nerve cells of the cochlea 140, and the excitation signals 332 comprising electrical stimulation signals provided by the electrode array to the auditory nerve cells of the cochlea 140. For another example, the apparatus 300 can function similarly to a traditional bone conduction auditory prosthesis, with the at least one excitation assembly 330 comprising a bone conduction actuator (e.g., a direct percutaneous implant and abutment; active or passive transcutaneous implant component), and the excitation signals 332 comprising sound vibrations provided by the bone conduction actuator and transmitted to the auditory system through the skull bones, such as through vibrating the bony structure of the cochlea. For another example, the apparatus 300 can function similarly to a traditional middle ear auditory prosthesis, with the at least one excitation assembly 330 comprising a middle ear actuator implanted in the middle ear region of the recipient, and the excitation signals 332 comprising mechanical stimulations delivered by the middle ear actuator to the middle or inner ear. For another example, the apparatus 300 can function similarly to a traditional direct acoustic cochlear implant, with the at least one excitation assembly 330 comprising a direct acoustic stimulator coupled to the cochlea 140, and the excitation signals 332 comprising vibrations delivered by the direct acoustic stimulator to the cochlea 140. For another example, the apparatus 300 can function similarly to a traditional auditory brainstem implant, with the at least one excitation assembly 330 comprising an electrode in electrical communication with acoustic nerves (e.g., the cochlear nucleus) of the brainstem, and the excitation signals 332 comprising electrical signals provided by the electrode to the acoustic nerves. Other types of auditory prostheses (e.g., apparatus 300), excitation assemblies 330, and excitation signals 332 are also compatible with certain embodiments described herein.

In certain embodiments, the apparatus 300 comprises other features and functionalities. The apparatus 300 of certain embodiments comprises a microcontroller (e.g., a processor integrated circuit) configured to monitor performance of and/or to provide signals to various components of the apparatus 300 (e.g., to adjust performance parameters of the at least one transmission circuit 310, the at least one detection circuit 320, the at least one excitation assembly 330, and/or one or more other components of the apparatus 300). In certain such embodiments, the apparatus 300 is configured to wirelessly communicate power, control signals and/or other information between an implantable portion of the auditory prosthesis and a non-implantable portion of the auditory prosthesis (e.g., via one or more implanted induction coils and one or more non-implantable induction coils). The apparatus 300 of certain embodiments comprises power storage circuitry (e.g., one or more batteries, rechargeable batteries, non-rechargeable batteries, capacitors, or other power storage devices) configured to store power and to provide the power to other components of the apparatus 300. The apparatus 300 of certain embodiments comprises power transmission circuitry configured to wirelessly transmit power to the transducer assembly (e.g., apparatus 200; ITEC microphone 110). For example, in certain embodiments in which the first electromagnetic signals 302 are configured to wirelessly transmit power to the transducer assembly, the power transmission circuitry can comprise the at least one transmission circuit 310.

Figure 6:
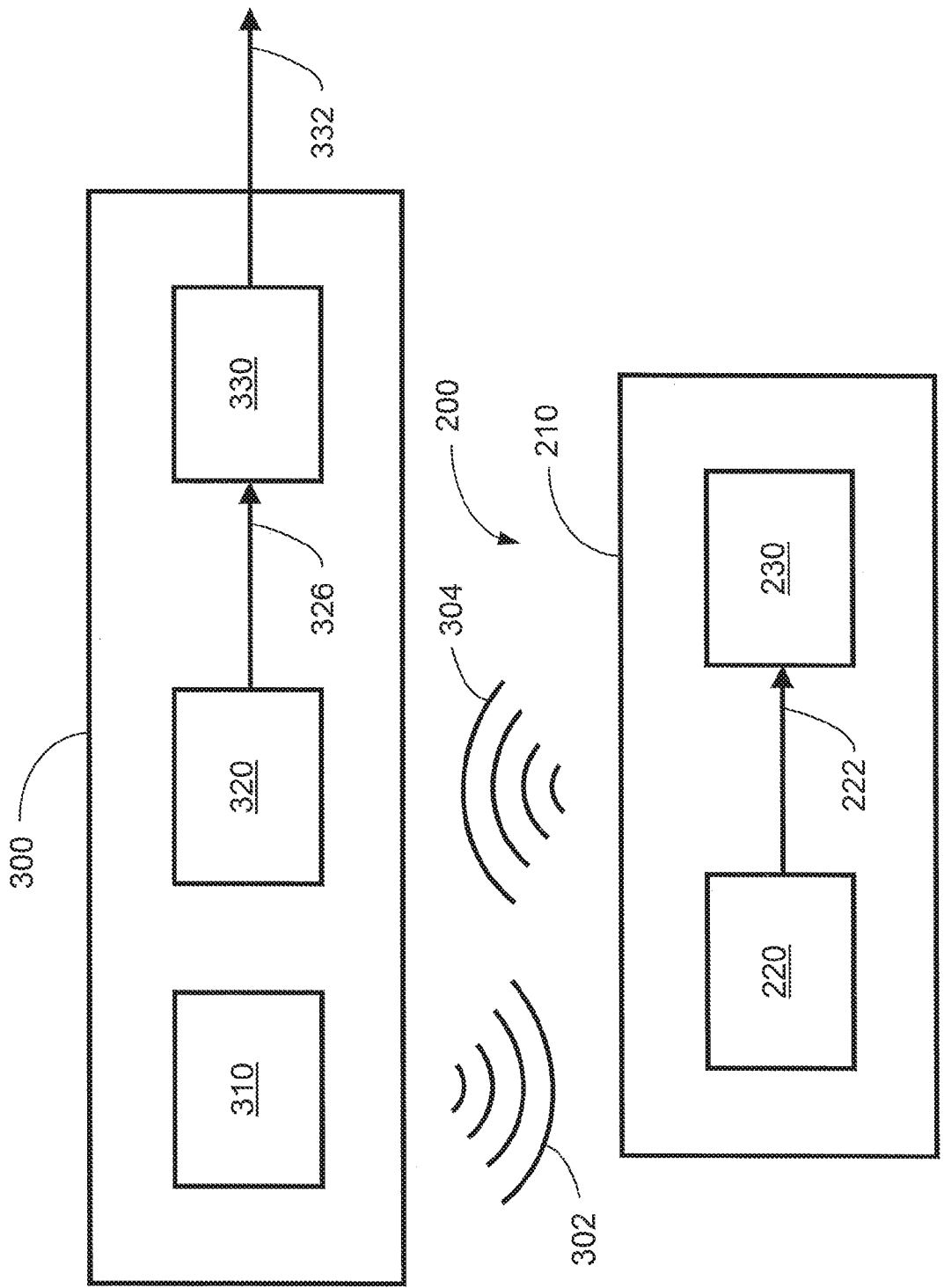
FIG. 6 schematically illustrates an example configuration (e.g., of an ITEC microphone and an implantable excitation device) in accordance with certain embodiments described herein.

FIG. 6 schematically illustrates an example configuration of an apparatus 200 (e.g., ITEC microphone 110) and an example apparatus 300 (e.g., implantable excitation device 120) in accordance with certain embodiments described herein. As described herein, in certain embodiments, at least one transducer 220 of the apparatus 200 (e.g., transducer assembly; ITEC microphone 110) generates output signals 222 indicative of the sound within the ear canal 102, and the at least one communication circuit 230 is configured to modulate at least one resonance frequency of the at least one communication circuit 230 in response to the output signals 222 from the at least one transducer 220. The carrier signal (e.g., the first electromagnetic signals 302) received by the apparatus 200 from the apparatus 300 can interact with the at least one communication circuit 230 to produce modulations of the second electromagnetic signals 304 radiated (e.g., backscattered) from the apparatus 200 and detected by the at least one detection circuit 320 of the apparatus 300. In certain embodiments, the output signals 222 from the at least one transducer 220 are indicative of the sound within the ear canal 102, the modulations of the at least one resonance frequency are in response to the output signals 222, the detected modulations of the second electromagnetic signals 304 are produced by the modulations of the at least one resonance frequency, and the excitation signals 332 are generated in response to the detected modulations of the second electromagnetic signals 304, so the excitation signals 332 are indicative of the sound within the ear canal 102.

The modulations of the resonance frequency can comprise at least one of: frequency modulations, amplitude modulations, phase modulations, and digital modulations. For example, the resonance frequency of the apparatus 200 can be modulated at a predetermined modulation frequency (different from the resonance frequency or the frequency of the carrier signal), resulting in modulations that are at the predetermined modulation frequency being applied to the second electromagnetic signals 304. Detecting the applied modulations at the apparatus 300 can then comprise detecting modulations of the portion of the second electromagnetic signals that are at the predetermined modulation frequency.

In certain embodiments, the apparatus 200 and the apparatus 300 are placed with well-defined distance, direction, and orientation between them, and the modulation scheme for the modulations applied by the apparatus to the second electromagnetic signals 304 (e.g., by modulating the at least one resonance frequency of the at least one communication circuit 230) is relatively simple. For example, various modulation schemes for the modulations applied by the apparatus 200 to the second electromagnetic signals 304 are compatible with certain embodiments described herein, including but not limited to: frequency modulation, amplitude modulation, phase modulation, and digital modulation.

In certain embodiments, by having the apparatus 200 apply modulations with a predetermined frequency to the second electromagnetic signals 304 and by having the apparatus 300 only accept signals having modulations with the predetermined frequency, certain embodiments described herein provide communications between the apparatus 200 and the apparatus 300 that are more robust (e.g., more resistant; less vulnerable) to noise or other interferences. For example, certain such embodiments reduce crosstalk between an apparatus 200/apparatus 300 system for the right ear and an apparatus 200/apparatus 300 system for the left ear. Furthermore, in certain embodiments, by having multiple parallel communication links between the apparatus 200 and the apparatus 300 carrying the same signal comprising information indicative of the detected sound, and having the apparatus 300 only accept signals that are the same on all the multiple parallel communication links, certain embodiments described herein provide communications between the apparatus 200 and the apparatus 300 that are more robust (e.g., more resistant; less vulnerable) to noise or other interferences. For example, two or more communication links can be operated simultaneously with one another, each having a different operating frequency of the carrier signal. For another example, two or three antennas with different radiation patterns (e.g., two or three coils mounted perpendicularly to one another) can be operated simultaneously with one another.

In certain embodiments, the energy transfer efficiency in the wireless communication link between the apparatus 200 and the apparatus 300 is selected to be sufficiently high to be robust to noise or other interferences and sufficiently low to not generate heat (due to absorption of the first electromagnetic signals 302 by tissue between the apparatus 200 and the apparatus 300) that causes significant damage or discomfort to the recipient. For example, the energy transfer efficiency can be about 10% (e.g., the power transmitted in the first electromagnetic signals 302 by the apparatus 300 being about 200 microwatts and the power received by the apparatus 200 being about 20 microwatts), in a range between 10% and 20%, and/or a range between 5% and 50%.

Figure 7A:
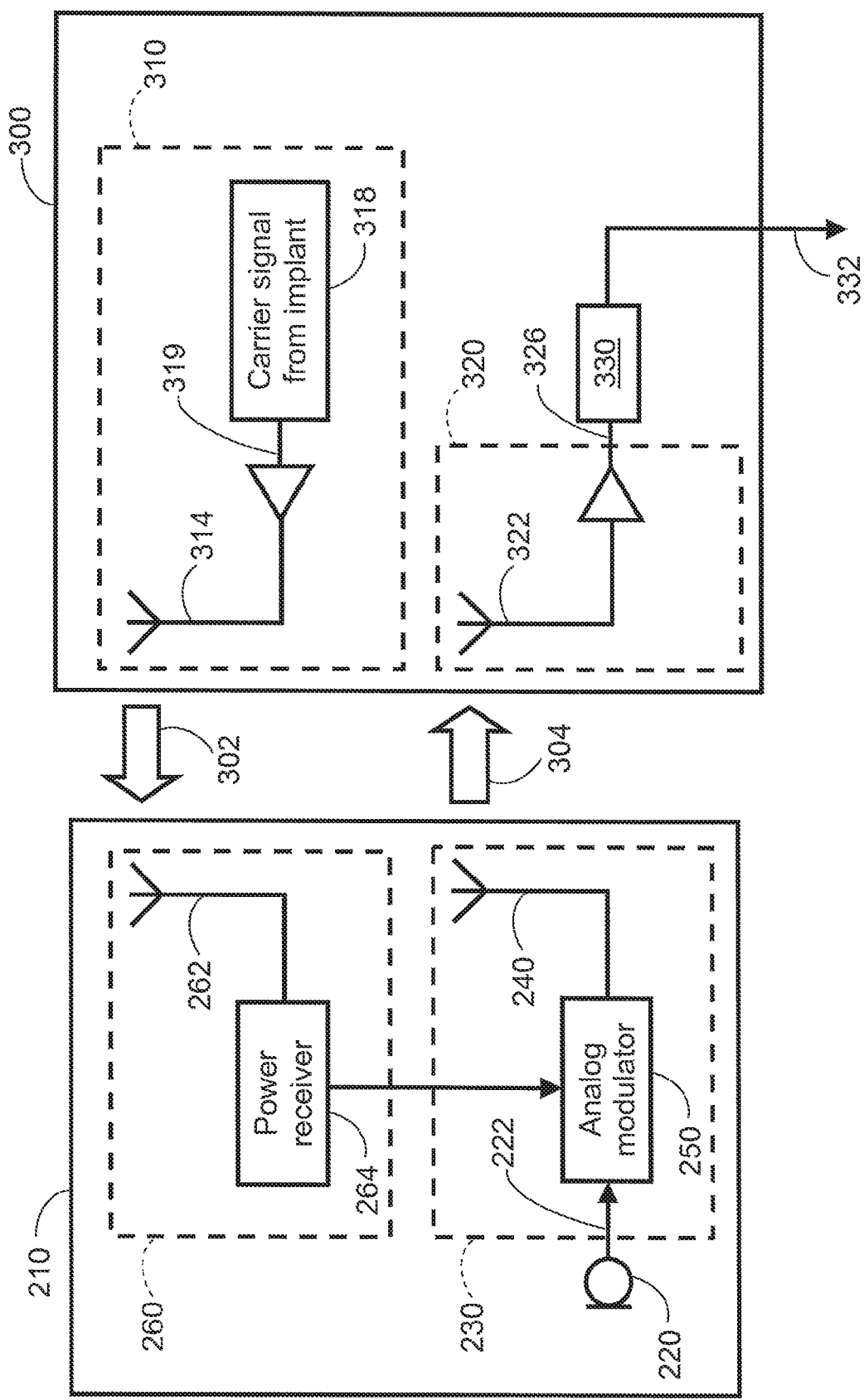
FIGS. 7A and 7B schematically illustrate two example configurations of an example ITEC microphone and an example implantable excitation device of an auditory prosthesis in accordance with certain embodiments described herein.
Figure 7B:
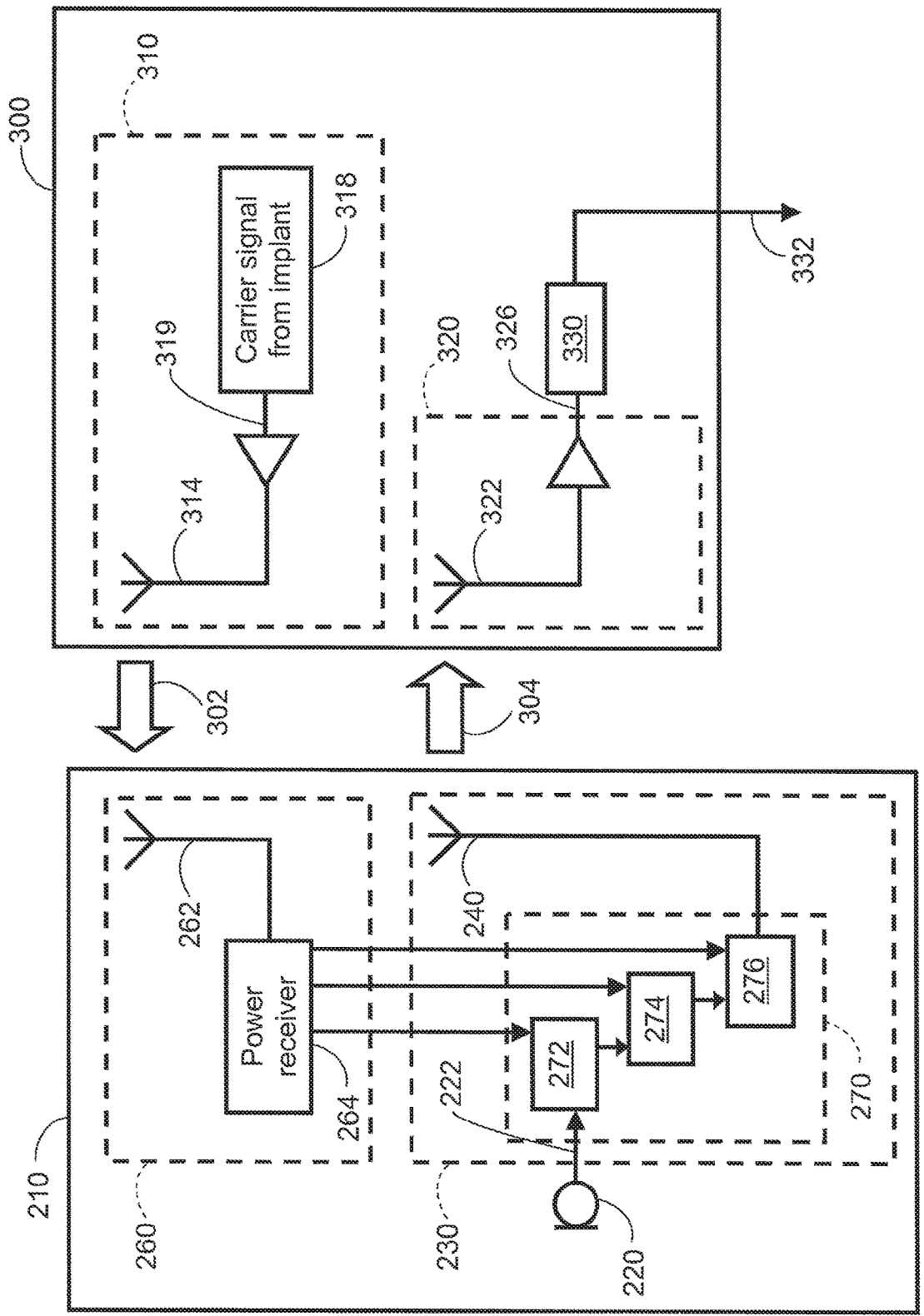

FIGS. 7A and 7B schematically illustrate two example configurations of an example apparatus 200 (e.g., ITEC microphone 110) and an example apparatus 300 (e.g., implantable excitation device 120 of an auditory prosthesis) in accordance with certain embodiments described herein. The apparatus 200 of FIGS. 7A and 7B is positioned within the ear canal 102 of the recipient and comprises a housing 210, a transducer 220 (e.g., passive microphone), and a communication circuit 230, with the communication circuit 230 comprising an antenna circuit 240 (e.g., comprising a coil) configured to wirelessly receive the first electromagnetic signals 302 (e.g., continuously transmitted carrier wave) that are wirelessly transmitted from the apparatus 300. The antenna circuit 240 can be weakly coupled to the first electromagnetic signals 302, and the modulations of the resonance frequency can generate second electromagnetic signals 304 comprising a modulated portion of the first electromagnetic signals 302 reflected back to the apparatus 300.

The apparatus 300 of FIGS. 7A and 7B comprises a transmission circuit 310 comprising a transmission antenna 314 (e.g., comprising a coil) and transmission circuitry 318 configured to provide input signals 319 (e.g., input carrier signal from the implantable auditory prosthesis) to the transmission antenna 314 which generates and wirelessly transmits the first electromagnetic signals 302 to the apparatus 200. The apparatus 300 further comprises a detection circuit 320 comprising a detection antenna 322 (e.g., comprising a coil) and configured to generate output signals 326 indicative of detected modulations of the second electromagnetic signals 304 and an excitation assembly 330 configured to generate excitation signals 332 indicative of the sound detected by the apparatus 200 in response to the output signals 326 from the detection circuit 320 and to provide the excitation signals 332 to the recipient's auditory system (e.g., to communicate the excitation signals 332 to the recipient).

While the example apparatus 300 of FIGS. 7A and 7B comprises two separate antennas, the transmission antenna 314 and the detection antenna 322, in certain other embodiments, the apparatus 300 comprises a single antenna that serves as both the transmission antenna 314 and the detection antenna 322 (e.g., as schematically illustrated by FIG. 5C). This single antenna can be configured to simultaneously continuously transmit the first electromagnetic signals 302 (e.g., a CW carrier wave) and receive the second electromagnetic signals 304 (e.g., backscattered signals from the apparatus 200).

The communication circuit 230 of FIG. 7A further comprises an analog modulator circuit 250 configured to receive the analog output signals 222 from the transducer 220 and to modulate a resonance frequency of the antenna circuit 240 in response to the output signals 222 (e.g., with the frequency of the modulation being proportional to the analog output signals 222 from the transducer 220) such that the second electromagnetic signals 304 are indicative of the sound detected by the apparatus 200. In certain such embodiments, the communication link between the apparatus 200 and the apparatus 300 of FIG. 7A is fully analog, and the power used by the system (e.g., apparatus 200 and apparatus 300) is low, particularly when the at least one transducer 220 comprises a passive microphone utilizing a piezoelectric material that does not utilize external power to generate an output signal.

The communication circuit 230 of FIG. 7B further comprises a digital circuit 270 comprising an analog-to-digital ("ADC") circuit 272, a coder circuit 274, and a modulator circuit 276. The ADC circuit 272 is configured to receive the analog output signals 222 from the transducer 220 and to generate and transmit digital signals to the coder circuit 274 in response to the analog output signals 222. The coder circuit 274 is configured to encode the digital signals while maintaining the information indicative of the sound detected by the transducer 220 and to transmit the encoded digital signals to the modulator 276. For example, the coder circuit 274 can apply error correction or other coding schemes to the digital signals to provide more robustness (e.g., more resistance; less vulnerability) to external electromagnetic disturbances, as compared to a fully analog link from the apparatus 200 to the apparatus 300. In certain embodiments, the apparatus 300 comprises decoding circuitry (e.g., in the in the detection circuit 320; in the excitation assembly 330) configured to decode the encoded digital signals received from the apparatus 200. The modulator 276 is configured to modulate the resonance frequency of the antenna circuit 240 in response to the encoded digital signals such that the second electromagnetic signals 304 are indicative of the sound detected by the apparatus 200.

In certain embodiments, the apparatus 200 of FIGS. 7A and 7B further comprises power reception circuitry 260 configured to extract electrical power from the first electromagnetic signals 302 wirelessly received from the apparatus 300 and to provide the power to power storage circuitry (not shown) or to other components of the apparatus 200. The power reception circuitry 260 can comprise a power receiving antenna 262 and a circuit 264 configured to receive electrical power from the power receiving antenna 262, to store the electrical power, and to provide the electrical power to the communication circuit 230 of the apparatus 200. For example, as schematically illustrated by FIG. 7A, the analog modulator circuit 250 can be configured to receive electrical power from the circuit 264. For another example, as schematically illustrated by FIG. 7B, the digital circuit 270 (e.g., each of the ADC circuit 272, the coder circuit 274, and the modulator 276) can be configured to receive electrical power from the circuit 264 and to use the power received from the first electromagnetic signals 302 to modulate the resonance frequency. While the digital circuit 270 (e.g., ADC circuit 272, the coder circuit 274, and the modulator 276) may utilize more electrical power than does the analog modulator circuit 250, in certain embodiments, the digital circuit 270 provides a greater robustness (e.g., greater resistance; less vulnerability) to noise and other interferences.

While the example apparatus 200 of FIGS. 7A and 7B comprises two separate antennas, the antenna circuit 240 and the power receiving antenna 262, in certain other embodiments, the apparatus 200 comprises a single antenna that serves as both the antenna circuit 240 and the power receiving antenna 262. This single antenna can be configured to simultaneously reflect a modulated backscattered portion of the first electromagnetic signals 302 (e.g., the modulated second electromagnetic signals 304) and receive the first electromagnetic signals 302 for extracting electrical power for powering the apparatus 200.

Figure 8A:
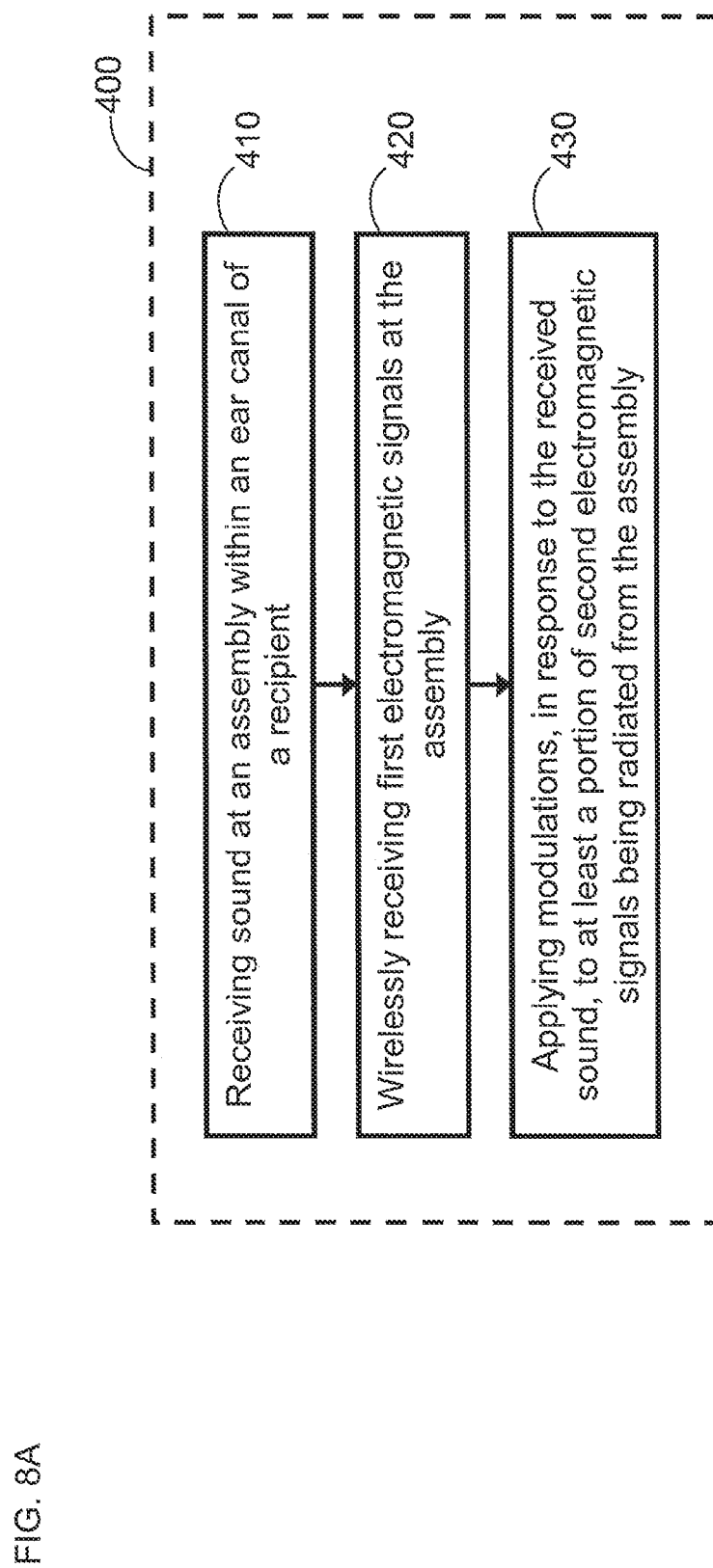
FIG. 8A is a flow diagram of an example method (e.g., utilizing an ITEC microphone) in accordance with certain embodiments described herein.

FIG. 8A is a flow diagram of an example method 400 in accordance with certain embodiments described herein. In an operational block 410, the method 400 comprises receiving sound at an assembly (e.g., ITEC microphone 110; apparatus 200) within an ear canal 102 of a recipient. In an operational block 420, the method 400 further comprises wirelessly receiving first electromagnetic signals 302 at the assembly within the ear canal 102. In an operational block 430, the method 400 further comprises applying modulations, in response to the received sound, to at least a portion of second electromagnetic signals 304 being radiated from the assembly (e.g., applying modulations to at least a portion of the first electromagnetic signals 302 back reflected from the assembly).

Figure 8B:
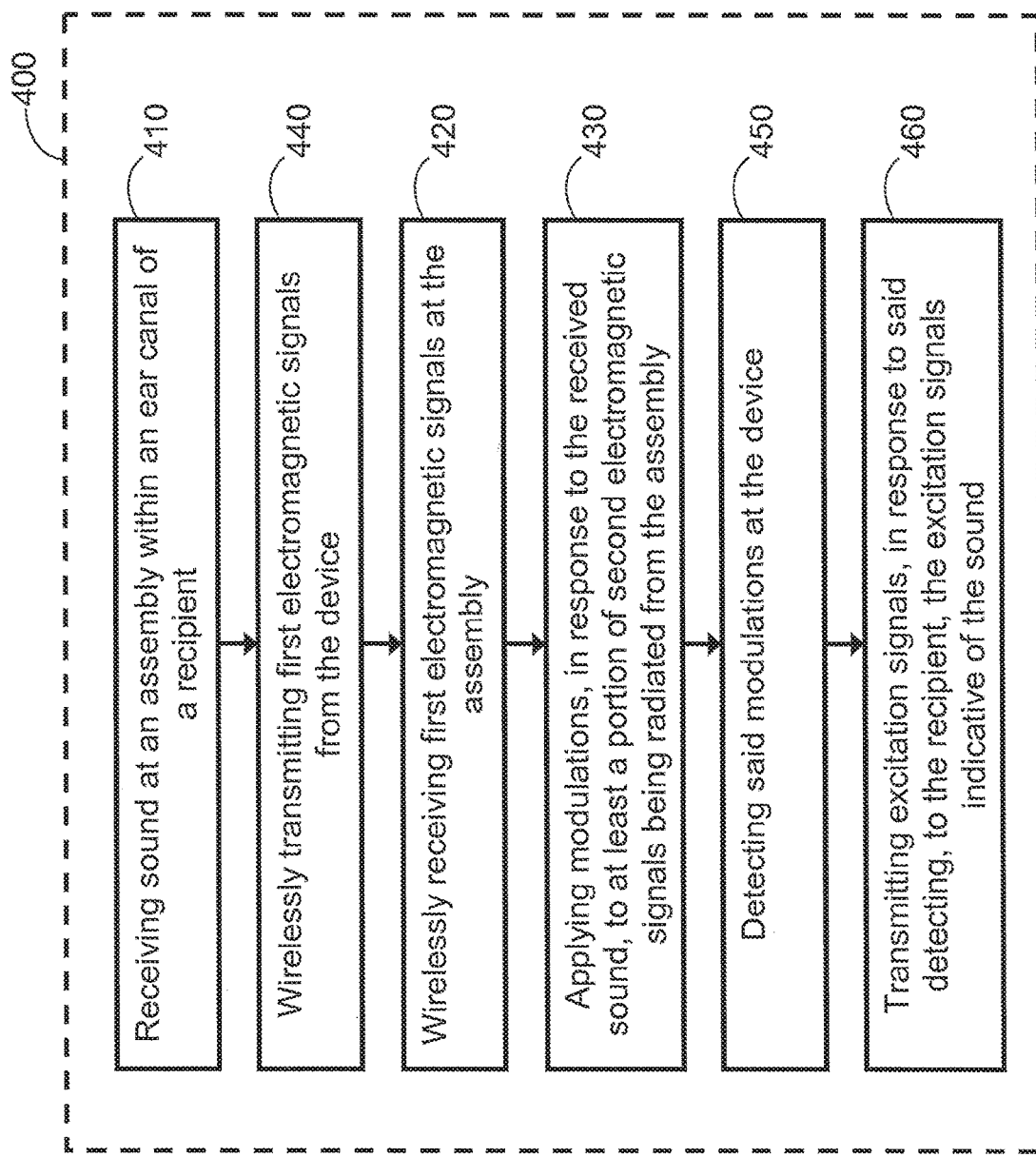
FIG. 8B is a flow diagram of another example method (e.g., utilizing an implantable excitation device) in accordance with certain embodiments described herein.

FIG. 8B is a flow diagram of another example method 400 in accordance with certain embodiments described herein. The method 400 of FIG. 8B comprises the operational blocks 410, 420, and 430 shown in FIG. 8C. In an operational block 440, the method 400 further comprises wirelessly transmitting the first electromagnetic signals 302 from a device (e.g., implantable excitation device 120; apparatus 300) implanted within a head of the recipient to the assembly (e.g., ITEC microphone 110; apparatus 200). In an operational block 450, the method 400 further comprises detecting said modulations at the device. In an operational block 460, the method 400 further comprises transmitting excitation signals, in response to said detecting, to the recipient, the excitation signals indicative of the sound.

In certain embodiments, applying modulations to the portion of the second electromagnetic signals 304 comprises modulating a resonance frequency of the assembly. The applied modulations of certain embodiments comprise at least one of: frequency modulations, amplitude modulations, phase modulations, and digital modulations. For example, the resonance frequency of the assembly can be modulated at a predetermined modulation frequency (different from the resonance frequency or the base frequency of the first electromagnetic signals 302) resulting in modulations at the predetermined modulation frequency applied to the portion of the second electromagnetic signals 304. Detecting the applied modulations at the device (e.g., implantable excitation device 120; apparatus 300) can then comprise detecting modulations of the portion of the second electromagnetic signals 304 that are at the predetermined modulation frequency.

Figure 9:
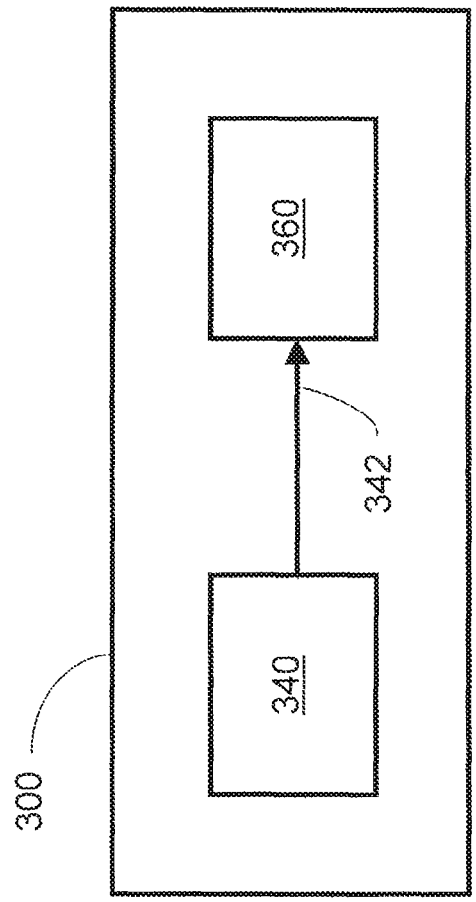
FIG. 9 schematically illustrates an example apparatus (e.g., an implantable excitation device) compatible with certain embodiments described herein.

In certain embodiments, the apparatus 300 (e.g., an implantable excitation device 120; a cochlear implant; a direct acoustic cochlear implant; a bone conduction auditory prosthesis; a middle ear auditory prosthesis; an auditory brainstem implant; any combination thereof) is configured to be implanted in the recipient and to communicate with a non-implantable transducer assembly (e.g., positionable within an ear canal 102 of a recipient; positionable externally to the recipient). FIG. 9 schematically illustrates an example apparatus 300 compatible with certain embodiments described herein. The apparatus 300 comprises at least one implantable communication circuit 340 configured to wirelessly receive signals (e.g., configured to use backscatter communications to wirelessly receive signals) from a transducer assembly positioned within an ear canal of a recipient (e.g., apparatus 200 comprising at least one transducer 220; ITEC microphone 110) or externally to the recipient. The at least one implantable communication circuit 340 is also configured to generate at least one detection signal 342 indicative of the wirelessly received signals from the transducer assembly. In certain embodiments, the at least one detection signal 342 is indicative of at least one of a presence and a strength of the wirelessly received signals from the transducer assembly. For example, the at least one implantable communication circuit 340 can generate the at least one detection signal 342 upon the at least one implantable communication circuit 340 wirelessly receiving signals from the transducer assembly (e.g., apparatus 200 comprising at least one transducer 220; ITEC microphone 110) with a signal strength greater than a predetermined signal strength. The at least one detection signal 342 thereby indicates that the transducer assembly is presently operational as an auditory prosthesis microphone (e.g., positioned within the ear canal 102 of the recipient or externally to the recipient at a proper location for operational communication with the apparatus 300 and capable of operational communication with the apparatus 300). Conversely, the at least one implantable communication circuit 340 can generate the at least one detection signal 342 upon the at least one implantable communication circuit 340 not wirelessly receiving signals from the transducer assembly or wirelessly receiving signals from the transducer assembly with a signal strength less than or equal to the predetermined signal strength. The at least one detection signal 342 thereby indicates that the transducer assembly is not presently operational as an auditory prosthesis microphone.

The apparatus 300 further comprises at least one implantable control circuit 360 (e.g., comprising a processor) configured to receive the at least one detection signal 342 and, in response to the at least one detection signal 342, to switch between a first state and a second state. The at least one implantable control circuit 360 in the first state (e.g., when a transducer assembly is presently operational as an auditory prosthesis microphone) is configured to control the apparatus 300 to use a first level of power, and the at least one implantable control circuit 360 in the second state (e.g., when a transducer assembly is not presently operational as an auditory prosthesis microphone) is configured to control the apparatus 300 to use a second level of power less than the first level of power. More specifically, in certain embodiments, the at least one implantable control circuit 360 in the first state is configured to control the apparatus 300 to use an operational level of power (e.g., a power level corresponding to full operation of the apparatus 300) and the at least one implantable control circuit 360 in the second state is configured to control the apparatus 300 to use a power-saving level of power (e.g., a power level corresponding to less-than-full operation of the apparatus 300) less than the operational level of power. For example, the at least one implantable control circuit 360 in the first state can control the at least one implantable communication circuit 340 to continually transmit carrier signals to the transducer assembly (e.g., for continual operation as an auditory prosthesis microphone), and the at least one implantable control circuit 360 in the second state can control the at least one implantable communication circuit 340 to intermittently transmit the carrier signals to the transducer assembly (e.g., to intermittently probe for an auditory prosthesis microphone).

In certain embodiments, the at least one implantable control circuit 360, in response to the at least one detection signal 342 indicating that the transducer assembly is not presently operational and/or in response to the at least one implantable control circuit 360 switching states (e.g., switching from the first state to the second state), is further configured to transmit an alert signal to an external device or directly to the recipient. The alert signal in some embodiments is transmitted instead of the at least one implantable control circuit 360 controlling the apparatus 300 to adjust the level of power in use (e.g., to use the second level of power instead of the first level of power). The alert signal is indicative of whether the at least one implantable control circuit 360 is in the first state or the second state. For example, the external device can be configured to communicate the state of the at least one implantable control circuit 360 to a caregiver of children or other recipients that may not be able to communicate themselves regarding the operational state of the apparatus 300. In some embodiments, direct communication to the recipient can include delivering a stimulation the auditory system with an intra-cochlear stimulating assembly, a bone conduction actuator coupled to the bony structure of the cochlea 140, a middle eat actuator coupled to the ossicular chain, or the cochlea 140, and so on. The stimulation delivered to the recipient in some embodiments includes a stored message, which takes the form of one or more beeps, clicks, words (e.g., 'your ear canal microphone is not presently operational') or other sounds depending on the embodiment.

In certain embodiments, the at least one implantable control circuit 360, in response to the at least one detection signal 342 indicating that the transducer assembly is not presently operational and/or in response to the at least one implantable control circuit 360 switching states (e.g., switching from the first state to the second state) and/or in response to the at least one implantable control circuit 360 transmitting the alert signal to an external device or to the recipient, the at least one implantable control circuit 360 is further configured to source one or more alternative transducer assemblies (e.g., microphones or other sources of audio). For instance, the at least one implantable control circuit 360 can initiate communications (e.g., RF communications via interface circuitry connected to the implantable coil 170 as described below, Bluetooth communications over a separate set of wireless communication components) with a paired external device that result in sound detected by a microphone embedded in, attached to or otherwise available to the paired external device being transmitted to the apparatus 300 for use in the generation of the perception of sound by the recipient. Further, the at least one implantable control circuit 360 can initiate additional or substitutional communications (e.g., RF communications via interface circuitry connected to the implantable coil 170 as described below, Bluetooth communications over a separate set of wireless communication components) with another device implanted in the recipient that result in sound detected by a microphone embedded in, attached to or otherwise available to the other implant being transmitted to the apparatus 300 for use in the generation of the perception of sound. In such embodiments, the apparatus 300 takes steps therefore to ensure that the recipient continues to perceive sound even when detection signal 342 does not indicate that the transducer assembly is presently operational as an auditory prosthesis microphone. The at least one implantable control circuit 360 sourcing one or more alternative transducer assemblies in some embodiments occurs instead of one or more of the at least one implantable control circuit 360 controlling the apparatus 300 to transmit an alert signal to an external device or directly to the recipient, the at least one implantable control circuit 360 controlling the apparatus 300 to adjust the level of power in use (e.g., to use the second level of power instead of the first level of power) and/or some other response.

Figure 10A:
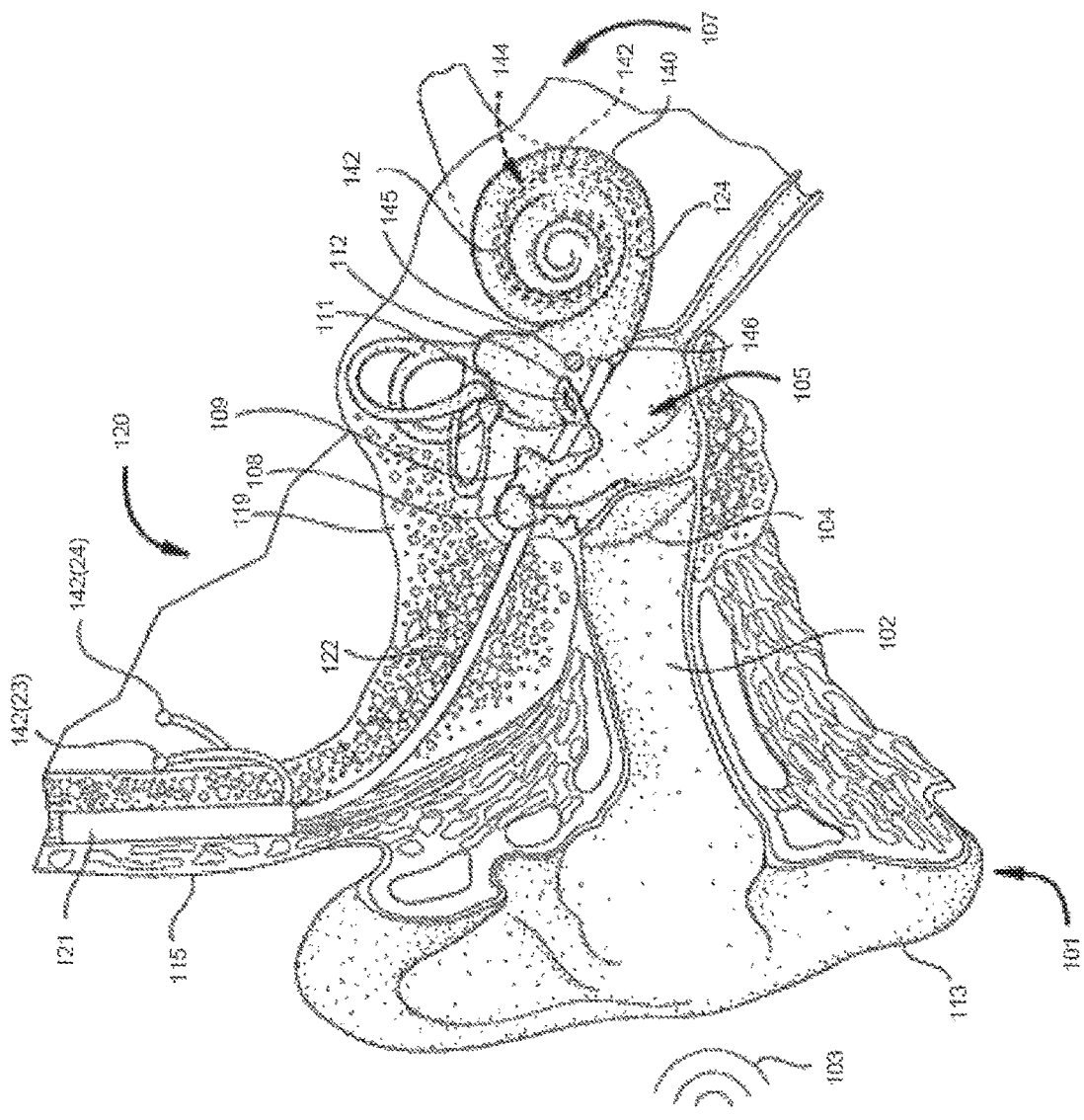

In certain embodiments, the implantable excitation device 120 comprises a "mostly implanted" cochlear implant ("MICI"). FIGS. 10A and 10B schematically illustrate an example MICI in accordance with certain embodiments described herein. Shown in FIG. 10A is an outer ear 101 (comprising an auricle 113 and an ear canal 102 in a fully functional human hearing anatomy), a tympanic membrane 104 disposed across the distal end of the ear canal 102, a middle ear 105 (comprising the malleus 108, the incus 109, and the stapes 111, collectively referred to as the ossicles 106, in a fully functional human hearing anatomy), and an inner ear 103 of the recipient. Sound signals 103, sometimes referred to herein as acoustic sounds or sound waves, are collected by the auricle 113 and channeled into and through the ear canal 102. The tympanic membrane 104 vibrates in response to the sound signals (e.g., sound waves) 103. This vibration is coupled to the oval window or fenestra ovalis 112 through the ossicles 106 which serve to filter and amplify the sound signals 103, causing oval window 112 to vibrate. Such vibration sets up waves of fluid motion within the cochlea 140 which, in turn, activates hair cells (not shown) that line the inside of the cochlea 140. Activation of these hair cells causes appropriate nerve impulses to be transferred through the spiral ganglion cells and the auditory nerve to the brain (not shown), where they are perceived as sound.

As noted above, sensorineural hearing loss may be due to the absence or destruction of the cochlea hair cells, which transduce acoustic signals into nerve impulses. One treatment for such hearing loss is a cochlear implant, which bypasses the cochlear hair cells and delivers stimulation (e.g., electrical stimulation) directly to the cochlea nerve cells. In the illustrative embodiment of FIGS. 10A and 10B, the implantable excitation device 120 of the cochlear implant comprises a MICI, meaning that most components of the cochlear implant configured to be implanted under the skin/tissue 115 of a recipient. In an embodiment, "most components" includes all components (as described below) necessary to function as an auditory prosthesis except the microphone (e.g., ITEC microphone 110). In such embodiments, none of the components of the MICI (e.g., implantable excitation device 120) and the microphone (e.g., ITEC microphone 110) must be visible on the recipient of such components through "casual inspection" by another person. Indeed, all of the components are either implanted in the recipient or disposed discretely in the ear canal 102 of the recipient. For instance, a cochlear implant consistent with embodiments described herein operates, for at least a finite period of time, from a charge stored by an internal power source (battery) 150, without the need of an external device except for the microphone (e.g., ITEC microphone 110). An external device can be used to, for example, charge the internal power source 150 of the cochlear implant from time to time as needed.

The implantable excitation device 120 comprises an implant body or main module 121, a lead region 122, and an elongate intra-cochlear stimulating assembly 124. In certain embodiments, the implant body 121 comprises a hermetically sealed housing 152 in which circuitry is disposed. For example, the circuitry disposed in the housing 152 can comprise the at least one transmission circuit 310, the at least one detection circuit 320, and the at least one excitation assembly 330 of FIG. 4. For another example, the circuitry disposed in the housing 152 can comprise the at least one implantable communication circuit 340 and the at least one implantable control circuit 360 of FIG. 9. In the example MICI of FIG. 10B, the circuitry disposed in the housing 152 comprises a transceiver unit 154 (e.g., comprising radio frequency (RF) interface circuitry comprising the at least one transmission circuit 310 and the at least one detection circuit 320), an implant control module 156 (e.g., comprising the at least one implantable control circuit 360), a sound processing unit 158, and a stimulator unit 160 (e.g., comprising the at least one excitation assembly 330) are disposed. For example, the sound processing unit 158 can be configured to receive signals from the transceiver unit 154 and, in response to control signals from the control module 156, to provide processed signals to the stimulator unit 160. While FIG. 10B shows at least one rechargeable power supply 150 (e.g., battery) outside the housing 152, in certain other embodiments, the power supply 150 (e.g., battery) can be within the housing 152. The housing 152 operates as a protective barrier between the electrical components within the housing 152 (e.g., in RF interface circuitry, battery, etc.) and the recipient's tissue and bodily fluid. For ease of illustration, electrical connections between the components within the housing 152 have been omitted from FIGS. 10A and 10B. In certain embodiments, the housing 152 (e.g., comprising the control module 156 and the power source 150) is implanted under the skin 115 of the skull, while in certain other embodiments, the housing 152 (e.g., comprising the control module 156 and the power source 150) is located in the middle ear cavity.

The implant body 121 also comprises one or more electrical components located outside (external to) the housing 152. The electrical components located outside the housing 152 include an internal/implantable coil 170, and the elongate intra-cochlear stimulating assembly 124. The RF interface circuitry is connected to the implantable coil 170 and, generally, a magnet (not shown) is fixed relative to the implantable coil 170. The implantable coil 170 is typically a wire antenna coil comprised of multiple turns of electrically insulated single-strand or multi-strand platinum or gold wire. In general, the implantable coil 170 and the RF interface circuitry enable the transfer of power and/or data from an external device (e.g., ITEC microphone 110) to the implantable excitation device 120. However, it is to be appreciated that various types of energy transfer, such as infrared (IR), electromagnetic, capacitive and inductive transfer, may be used to transfer power and/or data from an external device (e.g., ITEC microphone 110) to an implantable excitation device 120 and, as such, FIGS. 10A and 10B illustrates only one example arrangement. While FIGS. 10A and 10B correspond to a MICI which utilizes the intra-cochlear stimulating assembly 124 as an actuator, other configurations compatible with certain other embodiments can use other excitation devices besides the intra-cochlear stimulating assembly 124 (e.g., a bone conduction actuator coupled to the bony structure of the cochlea 140, a middle actuator coupled to the ossicular chain, or the cochlea 140.

Elongate stimulating assembly 124 is configured to be at least partially implanted in cochlea 140 and extends through an opening in the cochlea 140 (e.g., cochleostomy 146, oval window 112, the round window 145, etc.). The stimulating assembly 124 has a proximal end connected to the stimulator unit 160 via lead region 122 that extends through mastoid bone 119. Lead region 122 couples the stimulating assembly 124 to implant body 121 and, more particularly, to the stimulator unit 160. The stimulating assembly 124 includes a plurality of longitudinally spaced intra-cochlear electrical stimulating electrodes (electrodes) 142 that can be selectively used to deliver current to the cochlea 140. The stimulating electrodes 142 collectively form an intra-cochlear electrode array 144 that, in the example of FIG. 10A, comprises twenty-two (22) stimulating electrodes. Although FIG. 10A illustrates the use of twenty-two stimulating electrodes, is to be appreciated that different numbers, arrangements, etc., of intra-cochlear electrodes may be used in alternative embodiments. Also shown in FIG. 10A are two reference electrodes 142(23) and 142(24), located outside of the cochlear 140 and can also be used to deliver current to the recipient. Since the reference electrodes 142(23) and 142(24) are located outside of the cochlea 140, the reference electrodes are sometimes referred to as extra-cochlear electrodes (ECEs).

Figure 11:
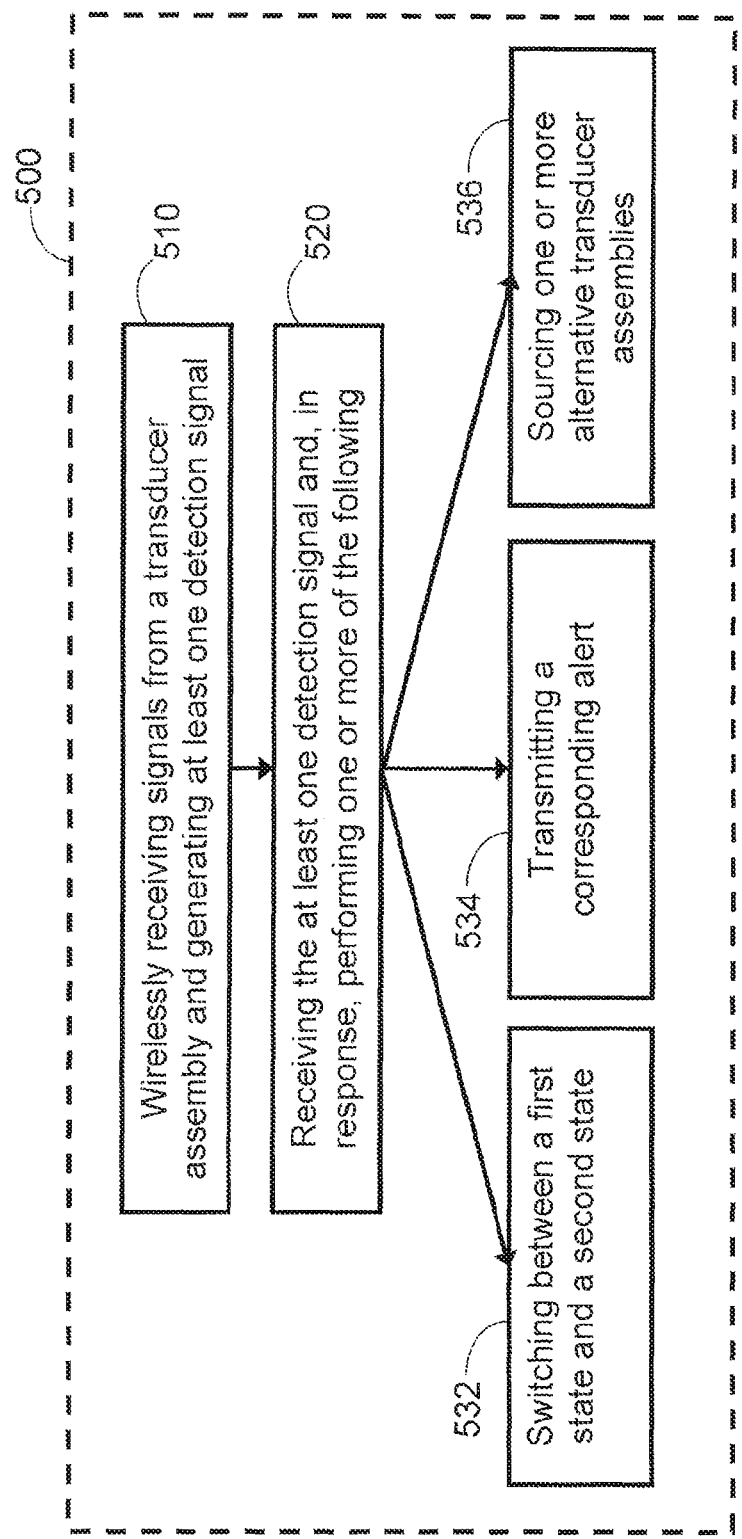
FIG. 11 is a flow diagram of an example method (e.g., utilizing an example implantable excitation device as shown in FIG. 9; utilizing an example MICI as shown in FIGS. 10A and 10B) in accordance with certain embodiments described herein.

FIG. 11 is a flow diagram of an example method 500 (e.g., utilizing an example implantable excitation device as shown in FIG. 9; utilizing an example MICI as shown in FIGS. 10A and 10B) in accordance with certain embodiments described herein. In an operational block 510, the method 500 comprises wirelessly receiving signals (e.g., using at least one implantable communication circuit 340) from a transducer assembly positioned within an ear canal of a recipient or externally to the recipient and generating at least one detection signal indicative of the wirelessly received signals from the transducer assembly. In an operational block 520, the method 500 further comprises receiving the at least one detection signal (e.g., using at least one implantable control circuit 360) and, in response to the at least one detection signal, performing one or more of the following: in an operational block 532, switching a circuit (e.g., the at least one implantable control circuit 360) between a first state and a second state, wherein the circuit in the first state is configured to control an apparatus (e.g., the example implantable excitation device; the example MICI) to use a first level of power, and the circuit in the second state is configured to control the apparatus to use a second level of power less than the first level of power; in an operational block 534, transmitting a corresponding alert to a destination external to the apparatus; and, in an operational block 536, sourcing one or more alternative transducer assemblies, wherein each of the one or more alternative transducer assemblies is separate from the transducer assembly positioned within the ear canal of the recipient or externally to the recipient.

It is to be appreciated that the embodiments disclosed herein are not mutually exclusive and may be combined with one another in various arrangements.

The invention described and claimed herein is not to be limited in scope by the specific example embodiments herein disclosed, since these embodiments are intended as illustrations, and not limitations, of several aspects of the invention. Any equivalent embodiments are intended to be within the scope of this invention. Indeed, various modifications of the invention in form and detail, in addition to those shown and described herein, will become apparent to those skilled in the art from the foregoing description. Such modifications are also intended to fall within the scope of the claims. The breadth and scope of the invention should not be limited by any of the example embodiments disclosed herein, but should be defined only in accordance with the claims and their equivalents.

CERTAIN EMBODIMENTS

Certain embodiments are listed below. The following embodiments are presented for explanatory and illustrative purposes only. It will be appreciated that the foregoing description is not limited to the following embodiments.

Embodiment 1

An apparatus comprising: a housing configured to be positioned within an ear canal of a recipient; at least one transducer positioned on or within the housing, the at least one transducer configured to respond to sound within the ear canal by generating output signals indicative of the sound; and at least one communication circuit having at least one resonance frequency, the at least one communication circuit positioned on or within the housing, the at least one communication circuit configured to receive the output signals from the at least one transducer and to modulate the at least one resonance frequency in response to the output signals from the at least one transducer.

Embodiment 2

The apparatus of Embodiment 1, wherein at least one transducer comprises a passive microphone.

Embodiment 3

The apparatus of Embodiment 1 or Embodiment 2, wherein the at least one communication circuit comprises at least one antenna circuit configured to wirelessly receive at least one signal from a device implanted in the recipient.

Embodiment 4

The apparatus of Embodiment 3, wherein the at least one antenna circuit has a radiation pattern that is rotationally symmetric about a direction parallel to a longitudinal axis of the housing.

Embodiment 5

The apparatus of Embodiment 3, wherein the at least one antenna circuit comprises a plurality of antenna circuits, each of which has a corresponding non-isotropic radiation pattern with a corresponding symmetry axis, wherein the symmetry axes are non-parallel to one another.

Embodiment 6

The apparatus of Embodiment 3, wherein the at least one communication circuit is configured to use power received from the at least one signal to modulate the at least one resonance frequency.

Embodiment 7

The apparatus of any of Embodiments 1 to 6, wherein the at least one communication circuit comprises a resonance circuit comprising an inductance L and a capacitance C, wherein the resonance frequency is dependent on the inductance L and the capacitance C, and wherein the at least one communication circuit is configured to modulate the at least one resonance frequency by modulating at least one of the inductance L and the capacitance C.

Embodiment 8

The apparatus of any of Embodiments 1 to 7, wherein the at least one communication circuit comprises a plurality of communication circuits, each of which has a corresponding resonance frequency and is configured to receive the output signals from the at least one transducer and to modulate the corresponding resonance frequency in response to the output signals from the at least one transducer.

Embodiment 9

An apparatus comprising: at least one transmission circuit configured to wirelessly transmit first electromagnetic signals to a transducer assembly positioned within an ear canal of a recipient; at least one detection circuit configured to detect second electromagnetic signals radiated from the transducer assembly, the second electromagnetic signals comprising a portion of the first electromagnetic signals reflected from the transducer assembly; and at least one excitation assembly configured to generate excitation signals in response to the second electromagnetic signals.

Embodiment 10

The apparatus of Embodiment 9, wherein the second electromagnetic signals comprise modulations that define data indicative of sound received by the transducer assembly, the at least one detection circuit is configured to detect said modulations, and the at least one excitation assembly is configured to generate excitation signals in response to said detected modulations.

Embodiment 11

The apparatus of Embodiment 9 or Embodiment 10, wherein the apparatus comprises an implantable auditory prosthesis, the transducer assembly comprises at least one electroacoustic transducer, and the at least one excitation assembly comprises at least one of: an electrode array, a middle ear actuator, a direct acoustic cochlear implant actuator, and a bone conduction actuator.

Embodiment 12

The apparatus of any of Embodiments 9 to 11, wherein the at least one detection circuit is configured to detect data indicative of sound received by the transducer assembly that is included within the second electromagnetic signals, and the excitation signals are indicative of the sound received by the transducer assembly and are configured to be communicated to the recipient.

Embodiment 13

The apparatus of any of Embodiments 9 to 12, wherein the at least one transmission circuit comprises at least one antenna configured to wirelessly transmit the first electromagnetic signals.

Embodiment 14

The apparatus of Embodiment 13, wherein the at least one antenna comprises a plurality of antenna circuits, each of which has a corresponding non-isotropic radiation pattern with a corresponding symmetry axis, wherein the symmetry axes are non-parallel to one another.

Embodiment 15

The apparatus of Embodiment 12 or Embodiment 13, wherein the at least one detection circuit comprises at least one detection antenna configured to receive the second electromagnetic signals radiated from the transducer assembly, the at least one detection antenna separate from the at least one antenna of the at least one transmission circuit.

Embodiment 16

A method comprising: receiving sound at an assembly within an ear canal of a recipient; wirelessly receiving first electromagnetic signals at the assembly within the ear canal; and in response to the received sound, applying modulations to at least a portion of second electromagnetic signals being radiated from the assembly.

Embodiment 17

The method of Embodiment 16, wherein said applying modulations comprises modulating a resonance frequency of the assembly.

Embodiment 18

The method of Embodiment 16 or Embodiment 17, wherein the second electromagnetic signals comprise a reflected portion of the first electromagnetic signals.

Embodiment 19

The method of any of Embodiments 16 to 18, further comprising: wirelessly transmitting the first electromagnetic signals from a device implanted within a head of the recipient to the assembly; detecting said modulations at the device; and in response to said detecting, transmitting excitation signals to the recipient, the excitation signals indicative of the sound.

Embodiment 20

The method of any of Embodiments 16 to 19, wherein said modulations comprise at least one of: frequency modulations, amplitude modulations, phase modulations, and digital modulations.

Embodiment 21

The method of Embodiment 20, wherein said modulations comprises modulations at a predetermined modulation frequency, and wherein said detecting said modulations comprises detecting modulations of the portion of the second electromagnetic signals at the predetermined modulation frequency.

Embodiment 22

An apparatus comprising: at least one implantable communication circuit configured to wirelessly receive signals from a transducer assembly positioned within an ear canal of a recipient or externally to the recipient and to generate at least one detection signal indicative of the wirelessly received signals from the transducer assembly; and at least one implantable control circuit configured to receive the at least one detection signal and, in response to the at least one detection signal, to perform one or more of the following: switch between a first state and a second state, wherein the at least one implantable control circuit in the first state is configured to control the apparatus to use a first level of power, the at least one implantable control circuit in the second state is configured to control the apparatus to use a second level of power less than the first level of power; transmit a corresponding alert to a destination external to the apparatus; and source one or more alternative transducer assemblies, wherein each of the one or more alternative transducer assemblies is separate from the transducer assembly positioned within the ear canal of the recipient or externally to the recipient.

Embodiment 23

The apparatus of Embodiment 22, wherein the at least one detection signal is indicative of at least one of a presence and a strength of the wirelessly received signals from the transducer assembly.

Embodiment 24

The apparatus of Embodiment 22 or Embodiment 23, wherein the at least one implantable control circuit in the first state is configured to control the apparatus to use an operational level of power and the at least one implantable control circuit in the second state is configured to control the apparatus to use a power-saving level of power less than the operational level of power.

Embodiment 25

The apparatus of Embodiment 22 or Embodiment 23, wherein the at least one implantable control circuit in the first state is configured to control the at least one implantable communication circuit to continually transmit carrier signals to the transducer assembly, and the at least one implantable control circuit in the second state is configured to control the at least one implantable communication circuit to intermittently transmit the carrier signals to the transducer assembly.

Embodiment 26

The apparatus of any of Embodiments 22 to 25, wherein the at least one implantable control circuit is further configured to transmit an alert signal to an external device, the alert signal indicative of whether the at least one implantable control circuit is in the first state or the second state.

Embodiment 27

The apparatus of Embodiment 22, wherein the destination external to the apparatus is a second apparatus separate from the transducer assembly and positioned externally to the recipient of the apparatus and the apparatus is configured to transmit the corresponding alert to the second apparatus.

Embodiment 28

The apparatus of Embodiment 22, wherein the destination external to the apparatus is the recipient and the apparatus is configured to transmit the corresponding alert to the recipient.

Embodiment 29

The apparatus of Embodiment 22, wherein the at least one implantable communication circuit is configured to use backscatter communications to wirelessly receive signals from the transducer assembly.

What is claimed is:

1. An apparatus comprising:
   a housing configured to be positioned within an ear canal of a recipient;
   at least one transducer positioned on or within the housing, the at least one transducer configured to respond to sound within the ear canal by generating output signals indicative of the sound; and
   at least one communication circuit having at least one resonance frequency, the at least one communication circuit positioned on or within the housing, the at least one communication circuit configured to receive the output signals from the at least one transducer and to modulate the at least one resonance frequency in response to the output signals from the at least one transducer, the at least one communication circuit comprising at least one antenna circuit configured to wirelessly receive at least one signal from a device implanted in the recipient.

2. The apparatus of claim 1, wherein at least one transducer comprises a passive microphone.

3. The apparatus of claim 1, wherein the at least one antenna circuit has a radiation pattern that is rotationally symmetric about a direction parallel to a longitudinal axis of the housing.

4. The apparatus of claim 1, wherein the at least one antenna circuit comprises a plurality of antenna circuits, each of which has a corresponding non-isotropic radiation pattern with a corresponding symmetry axis, wherein the symmetry axes are non-parallel to one another.

5. The apparatus of claim 1, wherein the at least one communication circuit is configured to use power received from the at least one signal to modulate the at least one resonance frequency.

6. The apparatus of claim 1, wherein the at least one communication circuit comprises a resonance circuit comprising an inductance L and a capacitance C, wherein the resonance frequency is dependent on the inductance L and the capacitance C, and wherein the at least one communication circuit is configured to modulate the at least one resonance frequency by modulating at least one of the inductance L and the capacitance C.

7. An apparatus comprising:
   a housing configured to be positioned within an ear canal of a recipient;
   at least one transducer positioned on or within the housing, the at least one transducer configured to respond to sound within the ear canal by generating output signals indicative of the sound; and
   at least one communication circuit having at least one resonance frequency, the at least one communication circuit positioned on or within the housing, the at least one communication circuit configured to receive the output signals from the at least one transducer and to modulate the at least one resonance frequency in response to the output signals from the at least one transducer, wherein the at least one communication circuit comprises a plurality of communication circuits, each of which has a corresponding resonance frequency and is configured to receive the output signals from the at least one transducer and to modulate the corresponding resonance frequency in response to the output signals from the at least one transducer.

8. An apparatus comprising:
   at least one transmission circuit configured to wirelessly transmit first electromagnetic signals to a transducer assembly positioned within an ear canal of a recipient;
   at least one detection circuit configured to detect second electromagnetic signals radiated from the transducer assembly, the second electromagnetic signals comprising a portion of the first electromagnetic signals reflected from the transducer assembly; and
   at least one excitation assembly configured to generate excitation signals in response to the second electromagnetic signals, wherein the apparatus comprises an implantable auditory prosthesis, the transducer assembly comprises at least one electroacoustic transducer, and the at least one excitation assembly comprises at least one of: an electrode array, a middle ear actuator, a direct acoustic cochlear implant actuator, and a bone conduction actuator.

9. The apparatus of claim 8, wherein the second electromagnetic signals comprise modulations that define data indicative of sound received by the transducer assembly, the at least one detection circuit is configured to detect said modulations, and the at least one excitation assembly is configured to generate excitation signals in response to said detected modulations.

10. The apparatus of claim 8, wherein the at least one detection circuit is configured to detect data indicative of sound received by the transducer assembly that is included within the second electromagnetic signals, and the excitation signals are indicative of the sound received by the transducer assembly and are configured to be communicated to the recipient.

11. The apparatus of claim 8, wherein the at least one transmission circuit comprises at least one antenna configured to wirelessly transmit the first electromagnetic signals.

12. The apparatus of claim 11, wherein the at least one detection circuit comprises at least one detection antenna configured to receive the second electromagnetic signals radiated from the transducer assembly, the at least one detection antenna separate from the at least one antenna of the at least one transmission circuit.

13. An apparatus comprising:
   at least one transmission circuit configured to wirelessly transmit first electromagnetic signals to a transducer assembly positioned within an ear canal of a recipient, the at least one transmission circuit comprising at least one antenna configured to wirelessly transmit the first electromagnetic signals, the at least one antenna comprising a plurality of antenna circuits, each of which has a corresponding non-isotropic radiation pattern with a corresponding symmetry axis, wherein the symmetry axes are non-parallel to one another;
   at least one detection circuit configured to detect second electromagnetic signals radiated from the transducer assembly, the second electromagnetic signals comprising a portion of the first electromagnetic signals reflected from the transducer assembly; and at least one excitation assembly configured to generate excitation signals in response to the second electromagnetic signals.

14. A method comprising:
receiving sound at an assembly comprising at least one electroacoustic transducer within an ear canal of a recipient;
wirelessly receiving first electromagnetic signals at the assembly within the ear canal; and
in response to the received sound, applying modulations to at least a portion of second electromagnetic signals being radiated from the assembly, wherein the second electromagnetic signals comprise a reflected portion of the first electromagnetic signals, wherein the first electromagnetic signals are received from an implantable auditory prosthesis comprising at least one excitation assembly configured to generate excitation signals in response to the second electromagnetic signals, the at least one excitation assembly comprising at least one of: an electrode array, a middle ear actuator, a direct acoustic cochlear implant actuator, and a bone conduction actuator.

15. The method of claim 14, wherein said applying modulations comprises modulating a resonance frequency of the assembly.

16. A method comprising:
receiving sound at an assembly within an ear canal of a recipient;
wirelessly receiving first electromagnetic signals at the assembly within the ear canal;
in response to the received sound, applying modulations to at least a portion of second electromagnetic signals being radiated from the assembly;
wirelessly transmitting the first electromagnetic signals from a device implanted within a head of the recipient to the assembly;
detecting said modulations at the device; and
in response to said detecting, transmitting excitation signals to the recipient, the excitation signals indicative of the sound.

17. The method of claim 16, wherein said modulations comprise at least one of: frequency modulations, amplitude modulations, phase modulations, and digital modulations.

18. The method of claim 17, wherein said modulations comprises modulations at a predetermined modulation frequency, and wherein said detecting said modulations comprises detecting modulations of the portion of the second electromagnetic signals at the predetermined modulation frequency.

19. An apparatus comprising:
at least one implantable communication circuit configured to wirelessly receive signals from a transducer assembly positioned within an ear canal of a recipient or externally to the recipient and to generate at least one detection signal indicative of the wirelessly received signals from the transducer assembly; and
at least one implantable control circuit configured to receive the at least one detection signal and, in response to the at least one detection signal, to perform one or more of the following:
switch between a first state and a second state, wherein the at least one implantable control circuit in the first state is configured to control the apparatus to use a first level of power, the at least one implantable control circuit in the second state is configured to control the apparatus to use a second level of power less than the first level of power;
transmit a corresponding alert to a destination external to the apparatus; and
source one or more alternative transducer assemblies, wherein each of the one or more alternative transducer assemblies is separate from the transducer assembly positioned within the ear canal of the recipient or externally to the recipient.

20. The apparatus of claim 19, wherein the at least one detection signal is indicative of at least one of a presence and a strength of the wirelessly received signals from the transducer assembly.

21. The apparatus of claim 19, wherein the at least one implantable control circuit in the first state is configured to control the apparatus to use an operational level of power and the at least one implantable control circuit in the second state is configured to control the apparatus to use a power-saving level of power less than the operational level of power.

22. The apparatus of claim 19, wherein the at least one implantable control circuit in the first state is configured to control the at least one implantable communication circuit to continually transmit carrier signals to the transducer assembly, and the at least one implantable control circuit in the second state is configured to control the at least one implantable communication circuit to intermittently transmit the carrier signals to the transducer assembly.

23. The apparatus of claim 19, wherein the at least one implantable control circuit is further configured to transmit an alert signal to an external device, the alert signal indicative of whether the at least one implantable control circuit is in the first state or the second state.

24. The apparatus of claim 19, wherein the destination external to the apparatus is a second apparatus separate from the transducer assembly and positioned externally to the recipient of the apparatus and the apparatus is configured to transmit the corresponding alert to the second apparatus.

25. The apparatus of claim 19, wherein the destination external to the apparatus is the recipient and the apparatus is configured to transmit the corresponding alert to the recipient.

26. The apparatus of claim 19, wherein the at least one implantable communication circuit is configured to use backscatter communications to wirelessly receive signals from the transducer assembly.

* * * * *